United States Patent
Wang et al.

(10) Patent No.: US 9,139,574 B2
(45) Date of Patent: Sep. 22, 2015

(54) TUMOR TARGETED DRUG COMBRETASTATIN A4 DERIVATIVE

(75) Inventors: Yong Wang, Nanjing (CN); Cang Zhang, Nanjing (CN); Xiaorong Liu, Nanjing (CN); Yan Zhang, Nanjing (CN); Yunyun Wang, Nanjing (CN); Wenping Zhang, Nanjing (CN)

(73) Assignee: Nanjing Sanhome Pharmaceutical Co., Ltd., Nanjing (CN)

( * ) Notice: Subject to any disclaimer, the term of this patent is extended or adjusted under 35 U.S.C. 154(b) by 0 days.

(21) Appl. No.: 14/127,847

(22) PCT Filed: Jul. 4, 2012

(86) PCT No.: PCT/CN2012/000921
§ 371 (c)(1),
(2), (4) Date: Dec. 19, 2013

(87) PCT Pub. No.: WO2013/004075
PCT Pub. Date: Jan. 10, 2013

(65) Prior Publication Data
US 2014/0128384 A1    May 8, 2014

(30) Foreign Application Priority Data

Jul. 5, 2011 (CN) .......................... 2011 1 0186688
Dec. 16, 2011 (CN) .......................... 2011 1 0422678

(51) Int. Cl.
| | |
|---|---|
| *C07D 413/04* | (2006.01) |
| *C07D 233/64* | (2006.01) |
| *C07D 263/32* | (2006.01) |
| *C07D 277/24* | (2006.01) |
| *C07C 251/24* | (2006.01) |
| *C07D 277/22* | (2006.01) |
| *A61K 31/53* | (2006.01) |

(52) U.S. Cl.
CPC ............ *C07D 413/04* (2013.01); *C07C 251/24* (2013.01); *C07D 233/64* (2013.01); *C07D 263/32* (2013.01); *C07D 277/22* (2013.01); *C07D 277/24* (2013.01)

(58) Field of Classification Search
CPC combination set(s) only.
See application file for complete search history.

(56) References Cited

U.S. PATENT DOCUMENTS

| | | | |
|---|---|---|---|
| 4,996,237 A | 2/1991 | Pettit et al. | |
| 5,561,122 A | 10/1996 | Pettit | |
| 5,674,906 A | 10/1997 | Hatanaka et al. | |
| 6,201,001 B1 * | 3/2001 | Wang et al. | 514/396 |

FOREIGN PATENT DOCUMENTS

| | | |
|---|---|---|
| CN | 101230074 A | 7/2008 |
| CN | 101230079 A | 7/2008 |
| CN | 101602730 A | 12/2009 |
| CN | 102190625 A | 9/2011 |
| EP | 1200412 A2 | 5/2002 |
| WO | 0109103 A2 | 2/2001 |

OTHER PUBLICATIONS

Yi et al. "Substituted Imidazole Derivative." CN 101602730 (Dec. 16, 2009) English machine translation.*
Wang et al. "Stillbene tumor targeted medicine Combretastatin A4 analaogs." CN 102190625 (Sep. 21, 2011) English machine translation.*
Romagnoli et al. "Convergent Synthesis and Biological Evaluation of 2-Amino-4-(30,40,50-trimethoxyphenyl)-5-aryl Thiazoles as Microtubule Targeting Agents" J. Med. Chem. 2011, 54, 5144-5153.*
Chongqin et al. "Substituted imidazole derivatives" CN 101602730 Dec. 16, 2009 (English machine translation).*
Chemical Abstract Service (CAS) STN Registry Database No. 1347389-28-9 [entered STN: Dec. 2, 2011].*
Chemical Abstract Service (CAS) STN Registry Database No. 1347294-03-4 [entered STN: Dec. 2, 2011].*
4-(3-Halo/amino-4,5-dimethoxyphenyl)-5-aryloxazoles and-N-methylimidazoles that are cytotoxic against combretastatin A Resistant Tumor Cells and Vascular Disrupting in a Cisplatin Resistant Germ Cell Tumor Model, J. Med. Chem. (2010): vol. 53, pp. 6595-6602.
Biersack et al., "Ru(h6-arene) complexes of combretastin-analogous oxazoles with enhanced anti-tumoral impact," European Journal of Medincial Chemistry (2010); vol. 45, pp. 4890-4896.
Ohsumi et al., "Syntheses and antitumor activity of cis-restricted combretastatins: 5-membered heterocyclic analogues," Bioorganic & Medicinal Chemistry Letters 8 (1998); pp. 3153-3158.
Wang et al., "Potent, Orally Active Heterocycle-Based Combretastatin A-4 Analogues: Synthesis, Structure-Activity Relationship, Pharmacokinetics, and In Vivo Antitumor Activity Evaluation," J. Med. Cham (2002): vol. 45, pp. 1697-1711.

* cited by examiner

*Primary Examiner* — Joseph Kosack
*Assistant Examiner* — Amanda L Aguirre
(74) *Attorney, Agent, or Firm* — Fox Rothschild LLP; Wansheng Jerry Liu

(57) ABSTRACT

The present invention relates to imidazole, oxazole and thiazole derivatives of tumor-targeted drug combretastatin A4, and phosphate esters, sulfonate esters or pharmaceutically acceptable salts, glycoside derivatives, solvates thereof, wherein the A-ring comprises a 3,5-dimethoxyphenyl group having a substituent at the 4-position. The pharmacological activity assays have demonstrated that the compounds of the present invention have good in vitro anti-tumor activity and excellent tubulin inhibitory effect.

11 Claims, 1 Drawing Sheet

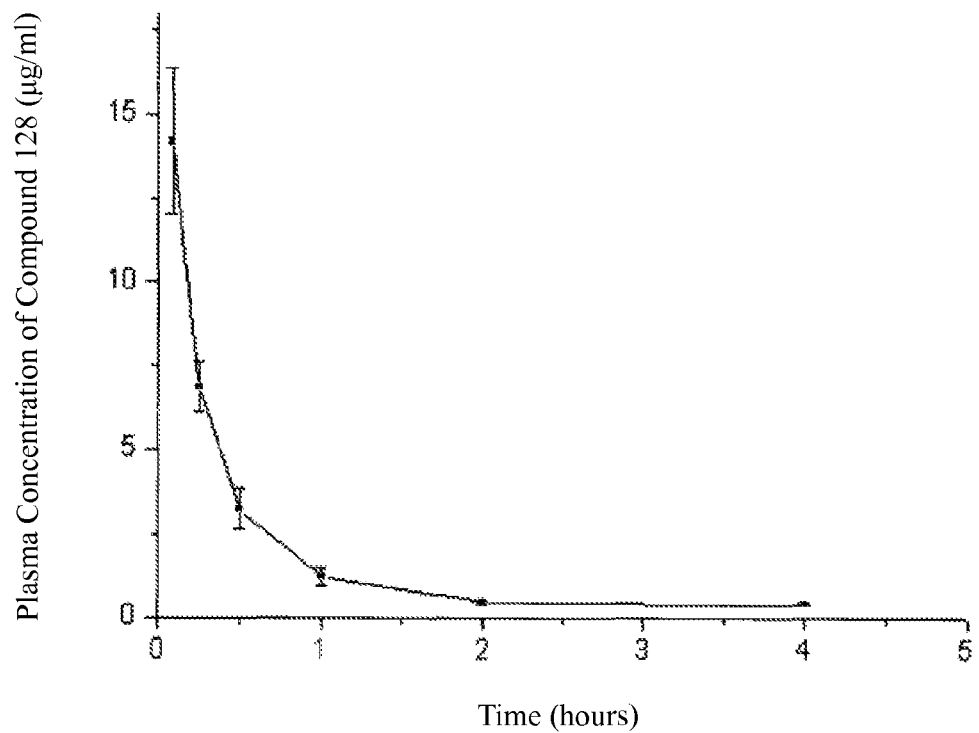

TUMOR TARGETED DRUG COMBRETASTATIN A4 DERIVATIVE

CROSS-REFERENCE TO RELATED APPLICATIONS

This application is the 35 U.S.C. §371 National Phase Application of International Application Serial No. PCT/CN2012/000921, filed on Jul. 4, 2012, which in turn claims priority to Chinese Patent Application No. CN 201110186688.3, filed on Jul. 5, 2011, and No. CN 201110422678.5, filed on Dec. 16, 2011, all of which are hereby incorporated by reference in their entireties.

FIELD OF THE INVENTION

The present invention relates to a new type of tumor-targeted drug combretastatin A4 derivatives, and preparation methods and medical uses thereof, as well as compositions comprising these compounds. The present invention belongs to the technical field of medicine.

BACKGROUND OF THE INVENTION

At present, a tubulin-binding agent, which generally exerts anticancer effects by depolymerizing or stabilizing microtubule, is one of the most effective anticancer drugs in clinical applications. Microtubule is an important component of cells, and constitutes mitotic apparatus. It involves cell movement, attachment and intracellular transport. Vinca alkaloids drugs, especially vincristine and vinblastine, have been clinically used for many years. In recent years, it is shown that vinorelbine can be used in the treatment of breast cancer, and the study of vinflunine has entered into the clinical trial stage. This class of drugs belongs to an anti-mitotic agent, and can inhibit assembly in mitosis. Besides, another class of clinical active drugs, such as paclitaxel, exerts its anticancer effect by promoting the formation of non-functional microtubules. Thus, the same anticancer effect can be achieved by interference with the tubulin using the drugs with totally different action mechanisms. Although these existing drugs are clinically active, they have poor efficacy on patients with advanced cancers, and may harm normal tissues. In recent years, a type of natural polyhydric stilbene compounds, combretastatin, which was isolated from the bark of African bush willow, has caused a lot of attention, among which the study of combretastatin A4 further clinically developed by Oxigene Company has made a promising progress.

Combretastatin A4 is the compound having the highest activity and the simplest structure in the combretastatin family. Studies have demonstrated that its possible mechanism of anticancer is binding rapidly with tubulin to realize the anti-mitotic function. Additionally, there are studies showing that this compound can target and destroy tumor cells without damaging blood vessels in normal tissues.

Combretastatin A4 has a basic structure of two benzene rings connected by an ethylene bridge, in which the one with three methoxy substituents is called ring A, and the other is called ring B. Its chemical name is cis-1-(3,4,5-trimethoxy phenyl)-2-(3'-hydroxy-4'-methoxy phenyl)ethylene. It can compete with colchicine for binding sites on tubulin. The currently available 1,2-stilbene derivatives are described in the existing publications, such as U.S. Pat. Nos. 4,996,237, 5,561,122 and 5,674,906, and the derivatives with 3,4,5-trimethoxyphenyl structure are described in De Martino, Gabriella et. al., *J. Med. Chem.* 2004, 47(25), 6120-6123.

Although combretastatin A4 has the cytotoxic activity and anti-tubulin polymerization activity in vitro, the cis-stilbene is structurally unstable and readily isomerizes into the trans-configuration. The cis-configuration, however, has stronger anti-tubulin activity than the trans-configuration. The structure-activity relationship indicates that the prerequisite for the activity is that the two benzene rings in the structure of combretastatin A4 take the cis-configuration. Accordingly, a series of analogues are obtained by replacing the ethenyl group with a rigid ring, such as a 4, 5 or 6-membered ring or a fused heterocyclic ring, so as to avoid the problem of stilbene isomerization and, in the meantime, retain substantially the cytotoxic activity and anti-tubulin polymerization activity of combretastatin A4. In addition, the A ring in the structure of combretastatin A4, i.e., the 3,4,5-trimethoxyphenyl group, is also necessary to maintain the high cytotoxic activity.

SUMMARY OF THE INVENTION

The objective of the present invention is to obtain the compounds with good inhibitory activity to tubulin by modifying the A ring into a 4-substituted 3,5-dimethoxy phenyl in addition to introducing a rigid ring, such as a five-membered ring, e.g., imidazole, oxazole, and thiazole, to replace the ethenyl group in the structure of combretastatin A4.

It is known that the A ring, i.e., 3,4,5-trimethoxyphenyl, in combretastatin A4 is necessary to maintain the high cytotoxic activity. However, the inventors of the present invention have found that the 3,5-dimethoxy phenyl A-ring having a substituent at 4-position also show excellent in vitro anticancer activity and tubulin inhibition.

The objective of the present invention is to provide a group of new tumor-targeted drug combretastatin A4 derivatives, namely, imidazole, oxazole, and thiazole compounds, wherein the A ring comprises the structure of a 4-substituted 3,5-dimethoxyphenyl group, having the structure of formula I:

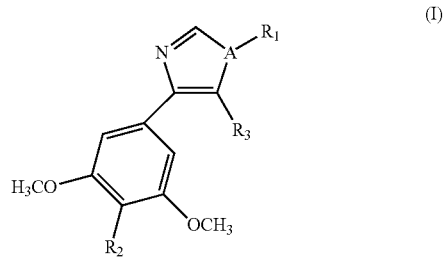

or phosphate esters, sulfonate esters, or pharmaceutically acceptable salts, glycoside derivatives, solvates thereof, wherein:

A is N, O or S;

when A is O or S, $R_1$ is absent;

when A is N, $R_1$ is H, $CH_3$, $C_4H_9$,

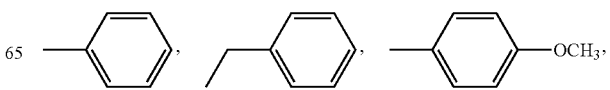

-continued
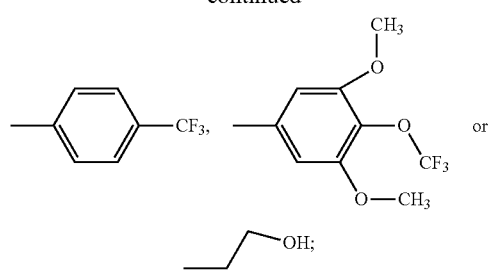
$R_2$ is H, F, Cl, Br, I, $OCH_3$, OH, $NO_2$, $NH_2$, $CF_3$, $OCF_3$, $OCHF_2$ or —$NHCH_3$;
$R_3$ is selected from the group consisting of:
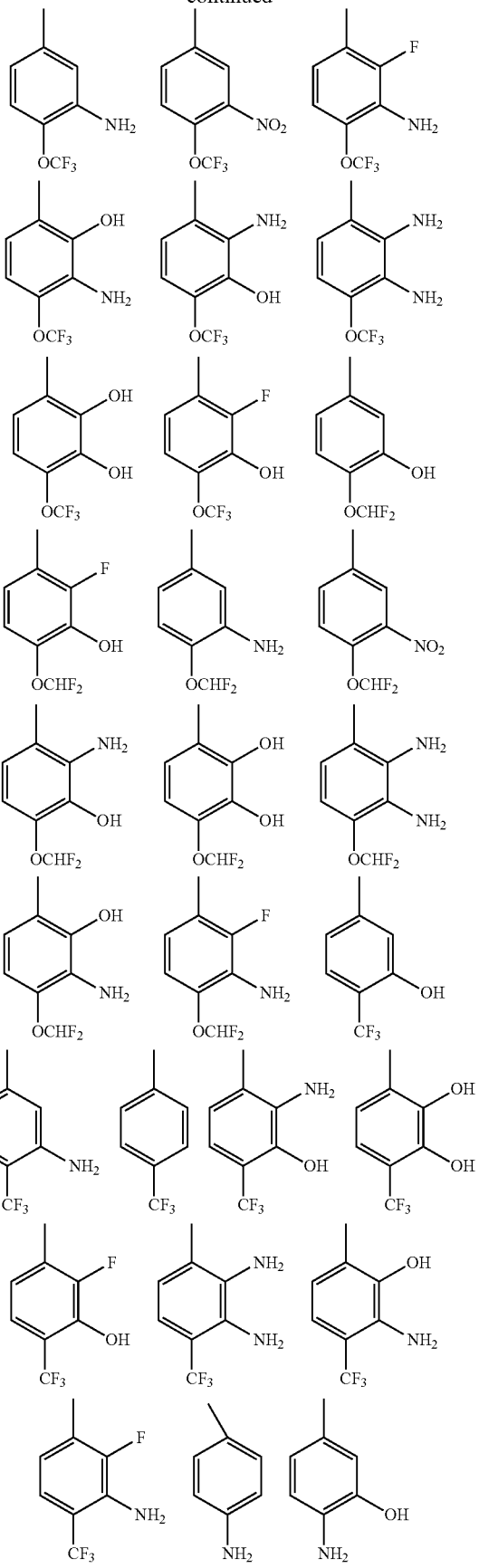

-continued 1) when A is N:
R$_1$ is CH$_3$, R$_2$ is H, and R$_3$ is 3,4,5-(OCH$_3$)$_3$C$_6$H$_2$, 4-N(CH$_3$)$_2$C$_6$H$_4$, 3-F-4-(OCH$_3$)C$_6$H$_3$, 3-(NH$_2$)-4-(OCH$_3$)C$_6$H$_3$ or 3,5-(OCH$_3$)$_2$-4-Br—C$_6$H$_2$;

R$_1$ is CH$_3$, C$_4$H$_9$, C$_6$H$_5$, R$_2$ is OCH$_3$, and R$_3$ is 3,4,5-(OCH$_3$)$_3$C$_6$H$_2$ or 4-pyridyl;

R$_1$ is CH$_3$, R$_2$ is OCH$_3$, and R$_3$ is 3-(NH$_2$)-4-(OCH$_3$)C$_6$H$_3$ or 4-N(CH$_3$)$_2$C$_6$H$_4$;

R$_1$ is CH$_3$, R$_2$ is Br, and R$_3$ is 3-F-4-(OCH$_3$)C$_6$H$_3$, 3-OH-4-(OCH$_3$)C$_6$H$_3$, 3-(NH$_2$)-4-(OCH$_3$)C$_6$H$_3$, 2,3-(OH)$_2$-4-(OCH$_3$)C$_6$H$_2$, 2-(NH$_2$)-3-OH-4-(OCH$_3$)C$_6$H$_2$ or 2-OH-3-(NH$_2$)-4-(OCH$_3$)C$_6$H$_2$;

R$_1$ is CH$_3$, R$_2$ is Cl, and R$_3$ is 3-(NH$_2$)-4-(OCH$_3$)C$_6$H$_3$ or 3-OH-4-(OCH$_3$)C$_6$H$_3$;

R$_1$ is CH$_3$, R$_2$ is OH, and R$_3$ is 3-OH-4-(OCH$_3$)C$_6$H$_3$;

R$_1$ is C$_4$H$_9$, C$_6$H$_5$, 4-methoxyphenyl, R$_2$ is H, and R$_3$ is 3,4,5-(OCH$_3$)$_3$C$_6$H$_2$ or 4-N(CH$_3$)$_2$C$_6$H$_4$;

R$_1$ is 4-methoxyphenyl, R$_2$ is OCH$_3$, and R$_3$ is 4-N(CH$_3$)$_2$C$_6$H$_4$;

R$_1$ is H, R$_2$ is OCH$_3$, and R$_3$ is 3-(NH$_2$)-4-(OCH$_3$)C$_6$H$_3$, 3-OH-4-(OCH$_3$)C$_6$H$_3$, 4-N(CH$_3$)$_2$C$_6$H$_4$ or 3-F-4-(OCH$_3$)C$_6$H$_3$; and R$_1$ is benzyl, R$_2$ is OCH$_3$, and R$_3$ is 3-F-4-(OCH$_3$)C$_6$H$_3$, 3-(OCH$_2$C$_6$H$_5$)-4-(OCH$_3$)C$_6$H$_3$ or 4-N(CH$_3$)$_2$C$_6$H$_4$;

2) when A is O:
R$_2$ is OCH$_3$, and R$_3$ is 3,4,5-(OCH$_3$)$_3$C$_6$H$_2$, 3-(NH$_2$)-4-(OCH$_3$)C$_6$H$_3$, 3-OH-4-(OCH$_3$)C$_6$H$_3$, 4-N(CH$_3$)$_2$C$_6$H$_4$ or 3-(OCH$_2$C$_6$H$_5$)-4-(OCH$_3$)C$_6$H$_3$; and R$_2$ is H, and R$_3$ is 3,5-(OCH$_3$)$_2$-4-Br—C$_6$H$_2$; and 3) when A is S:
R$_2$ is OCH$_3$, and R$_3$ is 3-(NH$_2$)-4-(OCH$_3$)C$_6$H$_3$.

Each of the groups in formula I mentioned above is preferably independently defined as follows:

A is preferably N;

R$_1$ is preferably

A and R$_1$ together are preferably O, NH or —NCH$_3$;

R$_2$ is preferably F, Cl, Br, I, OH, NO$_2$, NH$_2$, OCF$_3$, or OCHF$_2$;

R$_3$ is selected from the group consisting of:

In a preferred embodiment, the compounds of general formula I exclude the following compounds:

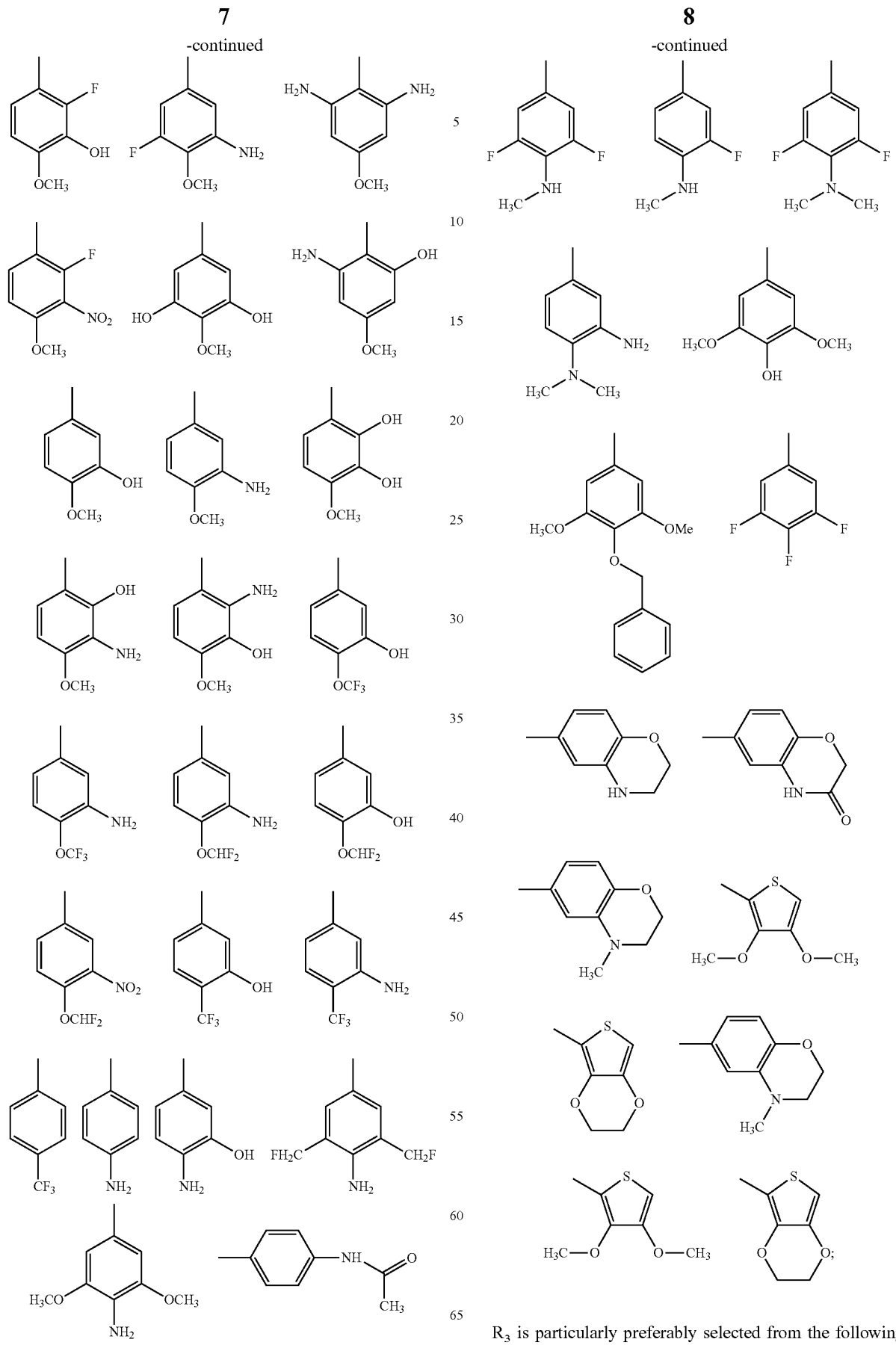
$R_3$ is particularly preferably selected from the following groups:

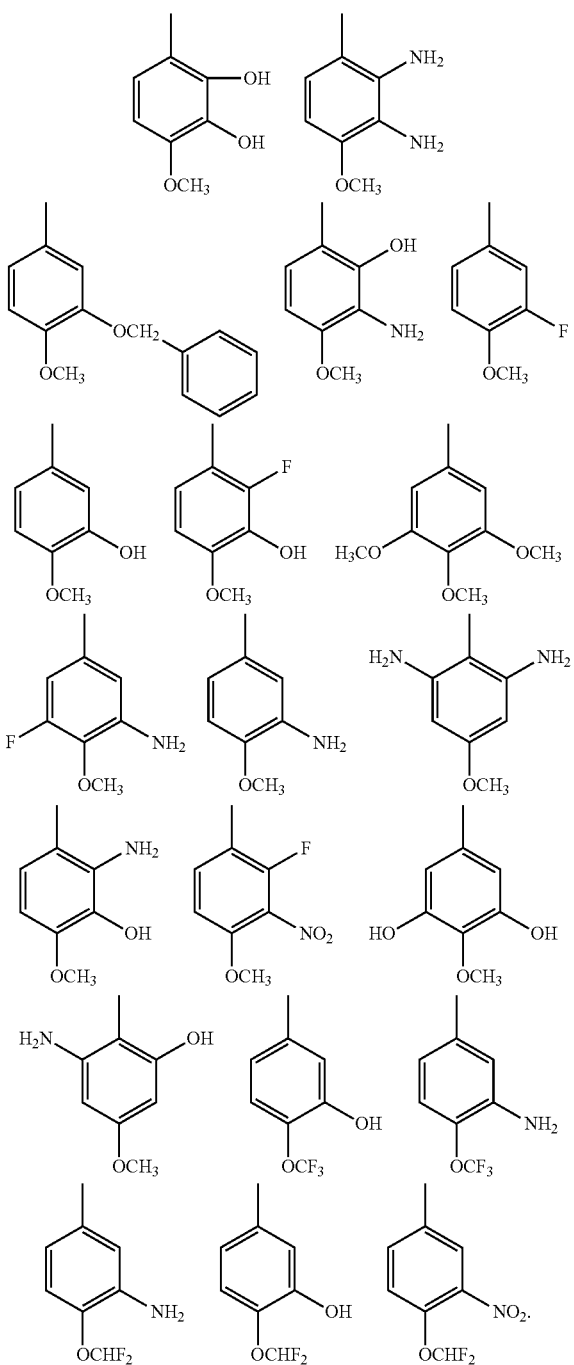

In a preferred embodiment, the present invention provides the following compounds:
5-(3-hydroxy-4-methoxyphenyl)-4-(3,5-dimethoxyphenyl)-1-(4-methoxyphenyl)imidazole (C074)
5-(4-dimethylaminophenyl)-4-(3,5-dimethoxyphenyl)-1-(4-trifluoromethylphenyl)imidazole (C088)
5-(3-hydroxy-4-methoxyphenyl)-4-(3,4,5-trimethoxyphenyl)-1-(4-trifluoromethylphenyl)imidazole (C077)
5-(3-hydroxy-4-methoxyphenyl)-4-(3,4,5-trimethoxyphenyl)-1-phenylimidazole (C087)
5-(3-hydroxy-4-methoxyphenyl)-4-(3,5-dimethoxyphenyl)-1-(4-trifluoromethylphenyl)imidazole (C081)
5-(3-hydroxy-4-methoxyphenyl)-4-(3,4,5-trimethoxyphenyl)-1-(4-methoxyphenyl)imidazole (C075)
5-(3-fluoro-4-methoxyphenyl)-4-(3,5-dimethoxyphenyl)-1-(3,4,5-trimethoxyphenyl)imidazole (C091)
5-(4-dimethylaminophenyl)-4-(3,4,5-trimethoxyphenyl)-1-(4-trifluoromethylphenyl)imidazole (C092)
5-(3,4,5-trimethoxyphenyl)-4-(3,5-dimethoxyphenyl)-1-(4-trifluoromethylphenyl)imidazole (C093)
5-(4-dimethylaminophenyl)-4-(3,5-dimethoxyphenyl)-1-(3,4,5-trimethoxyphenyl)imidazole (C098)
5-(3,4,5-trimethoxyphenyl)-4-(3,4-dimethoxyphenyl)-1-(3,4,5-trimethoxyphenyl)imidazole (C104)
5-(4-dimethylaminophenyl)-4-(3,4,5-trimethoxyphenyl)-1-(3,4,5-trimethoxyphenyl)imidazole (C106)
5-(3-hydroxy-4-methoxyphenyl)-4-(3,4,5-trimethoxyphenyl)-1-(3,4,5-trimethoxyphenyl)imidazole (C105)
5-(3,4,5-trimethoxyphenyl)-4-(3,4,5-trimethoxyphenyl)-1-(3,4,5-trimethoxyphenyl)imidazole (C107)
5-(4-Acetamidophenyl)-4-(3,5-dimethoxyphenyl)oxazole (C109)
4-(3,5-dimethoxyphenyl)-5-(3-hydroxy-4-methoxyphenyl)oxazole (C110)
4-(3,5-dimethoxyphenyl)-5-(4-aminophenyl)oxazole (C112)
4-(3,5-dimethoxyphenyl)-5-(3-amino-4-dimethylaminophenyl)oxazole (C113)
4-(3,5-dimethoxyphenyl)-5-(3-amino-4-methoxy-5-fluorophenyl)oxazole (C114)
4-(3,5-dimethoxyphenyl)-5-(3-amino-4-methoxyphenyl)oxazole (C115)
4-(3,5-dimethoxyphenyl)-5-(2,3-dihydroxy-4-methoxyphenyl)oxazole (C116)
4-(3,5-dimethoxyphenyl)-5-(2-fluoro-3-hydroxy-4-methoxyphenyl)oxazole (C117)
4-(3,5-dimethoxyphenyl)-5-(2,5-diamino-4-methoxyphenyl)oxazole (C119)
4-(3,5-dimethoxyphenyl)-5-(2,3-diamino-4-methoxyphenyl)oxazole (C121)
4-(3,5-dimethoxyphenyl)-5-(3-hydroxy-4-methylaminophenyl)oxazole (C123)
4-(3,5-dimethoxyphenyl)-5-(2-amino-3-hydroxy-4-methoxyphenyl)oxazole (C124)
4-(3,5-dimethoxyphenyl)-5-(3-amino-4-trifluoromethoxyphenyl)oxazole (C131)
4-(3,5-dimethoxyphenyl)-5-(3-amino-4-difluoromethoxyphenyl)oxazole (C133)
4-(3,5-dimethoxyphenyl)-5-(2-hydroxy-4-methoxy-5-aminophenyl)oxazole (C137)
4-(3,5-dimethoxyphenyl)-5-(3-amino-4-trifluoromethoxyphenyl)-1-methylimidazole (C132)
4-(3,5-dimethoxyphenyl)-5-(3-amino-4-difluoromethoxyphenyl)-1-methylimidazole (C135)
4-(3,5-dimethoxyphenyl)-5-(2-fluoro-3-amino-4-methoxyphenyl)-1-methylimidazole (C136)
4-(3,5-dimethoxyphenyl)-5-(3-hydroxy-4-methoxyphenyl)imidazole (C118)
4-(3,5-dimethoxyphenyl)-5-(3-fluoro-4-methoxyphenyl)imidazole (C128)
4-(3,5-dimethoxyphenyl)-5-(3-amino-4-methoxyphenyl)imidazole (C129)
4-(3,5-dimethoxyphenyl)-5-(4-dimethylaminophenyl)imidazole (C130)
N-methyl-4-(3,5-dimethoxyphenyl)-5-[(3,4-ethylenedioxyl)thienyl]imidazole (C238)
N-methyl-4-(3,5-dimethoxyphenyl)-5-[6-(3-oxobenzomorpholinyl)]imidazole (C252)
4-(3,5-dimethoxyphenyl)-5-[6-(3-oxobenzomorpholiny)]oxazole (C253)

N-methyl-4-(3,5-dimethoxyphenyl)-5-(6-benzomorpholinyl)-imidazole (C254)
4-(3,5-dimethoxyphenyl)-5-(6-benzomorpholinyl)oxazole (C255)
N-hydroxyethyl-4-(3,5-dimethoxyphenyl)-5-(3-fluoro-4-methoxyphenyl)imidazole (C256)
N-hydroxyethyl-4-(3,5-dimethoxyphenyl)-5-[(3,4-ethylenedioxyl)thienyl]imidazole (C257)
N-benzyl-4-(3,5-dimethoxyphenyl)-5-[(3,4-ethylenedioxyl)thienyl]imidazole (C258)
N-methyl-4-(3,5-dimethoxyphenyl)-5-(3,4,5-trifluorophenyl)imidazole (C262)
N-methyl-4-(3,5-dimethoxyphenyl)-5-(3,5-difluoro-4-methylaminophenyl)imidazole (C263)
4-(3,5-dimethoxyphenyl)-5-(3-fluoro-4-methylaminophenyl)oxazole (C264)
N-methyl-4-(3,5-dimethoxyphenyl)-5-[6-benzo(N-methylmorpholine)]imidazole (C265)
4-(3,5-dimethoxyphenyl)-5-[6-benzo(N-methylmorpholine)]oxazole (C266)
4-(3,5-dimethoxyphenyl)-5-(3-fluoro-4-methylaminophenyl)imidazole (C267)
N-methyl-4-(3,4,5-trimethoxyphenyl)-5-[(3,4-dimethoxy)thienyl]imidazole (C259)
N-hydroxyethyl-4-(3,4,5-trimethoxyphenyl)-5-[(3,4-dimethoxy)thienyl]imidazole (C260)
N-benzyl-4-(3,4,5-trimethoxyphenyl)-5-[(3,4-dimethoxy)thienyl]imidazole (C261)
N-hydroxyethyl-4-(3,4,5-trimethoxyphenyl)-5-(4-trifluoromethylphenyl)imidazole (C239)
N-methyl-4-(3,4,5-trimethoxyphenyl)-5-(4-trifluoromethylphenyl)imidazole (C240)
N-butyl-4-(3,4,5-trimethoxyphenyl)-5-(4-trifluoromethylphenyl)imidazole (C242)
N-cyclopropyl-4-(3,4,5-trimethoxyphenyl)-5-(4-trifluoromethylphenyl)imidazole (C243)
4-(3,4,5-trimethoxyphenyl)-5-(4-trifluoromethylphenyl)thiazole (C244)
N-ethoxycarbonylmethyl-4-(3,4,5-trimethoxyphenyl)-5-(4-trifluoromethylphenyl)imidazole (C245)
N-hydroxyethyl-4-(3,4,5-trimethoxyphenyl)-5-[(3,4-ethylenedioxyl)thienyl]imidazole (C246)
N-benzyl-4-(3,4,5-trimethoxyphenyl)-5-[(3,4-ethylenedioxyl)thienyl]imidazole (C247)
N-hydroxyethyl-4-(3,4,5-trimethoxyphenyl)-5-[4-(2,2'-dichlorodiethylamine)phenylimidazole (C248)
N-methyl-4-(3,4,5-trimethoxyphenyl)-5-[6-(3-oxobenzomorpholine)]imidazole (C249)
N-hydroxyethyl-4-(3,4,5-trimethoxyphenyl)-5-[6-(3-oxobenzomorpholinyl)]imidazole (C250)
N-methyl-4-(3,4,5-trimethoxyphenyl)-5-(6-benzomorpholinyl)imidazole (C251)
4-(3,5-dimethoxyphenyl)-5-(2-hydroxy-3-amino-4-methoxyphenyl)oxazole (C141)
4-(3,5-dimethoxyphenyl)-5-(3-hydroxy-4-trifluoromethoxyphenyl)oxazole (C142)
4-(3,5-dimethoxyphenyl)-5-(3-hydroxy-4-difluoromethoxyphenyl)oxazole (C143)
4-(3,5-dimethoxyphenyl)-5-(2-hydroxy-3-hydroxy-4-methoxyphenyl)imidazole (C144)
4-(3,5-dimethoxyphenyl)-5-(2-amino-3-amino-4-methoxyphenyl)imidazole (C145)
4-(3,5-dimethoxyphenyl)-5-(2-hydroxy-3-amino-4-methoxyphenyl)imidazole (C146)
4-(3,5-dimethoxyphenyl)-5-(2-amino-3-hydroxy-4-methoxyphenyl)imidazole (C147)
4-(3,5-dimethoxyphenyl)-5-(2-fluoro-3-hydroxy-4-methoxyphenyl)imidazole (C148)
4-(3,5-dimethoxyphenyl)-5-(2-fluoro-3-amino-4-methoxyphenyl)imidazole (C149)
4-(3,5-dimethoxyphenyl)-5-(3-hydroxy-4-trifluoromethoxyphenyl)imidazole (C150)
4-(3,5-dimethoxyphenyl)-5-(3-hydroxy-4-difluoromethoxyphenyl) imidazole (C151)
4-(3,5-dimethoxyphenyl)-5-(3-amino-4-trifluoromethoxyphenyl)imidazole (C152)
4-(3,5-dimethoxyphenyl)-5-(3-amino-4-difluoromethoxyphenyl)imidazole (C153)
4-(3,5-dimethoxy-4-aminophenyl)-5-(3-fluoro-4-methoxyphenyl)oxazole (CN01)
4-(3,5-dimethoxy-4-hydroxyphenyl)-5-(3-fluoro-4-methoxyphenyl)oxazole (CN03)
4-(3,5-dimethoxy-4-bromophenyl)-5-(3-hydroxy-4-methoxyphenyl)oxazole (CN02)
4-(3,5-dimethoxy-4-bromophenyl)-5-(3-amino-4-methoxyphenyl)oxazole (CN04)
4-(3,5-dimethoxy-4-hydroxyphenyl)-5-(3-amino-4-methoxyphenyl)oxazole (CN05)
4-(3,5-dimethoxy-4-hydroxyphenyl)-5-(3-hydroxy-4-methoxyphenyl)oxazole (CN06)
4-(3,5-dimethoxy-4-nitrophenyl)-5-(3-hydroxy-4-methoxyphenyl)oxazole (CN07)
4-(3,5-dimethoxy-4-aminophenyl)-5-(3-hydroxy-4-methoxyphenyl)oxazole (CN08)
4-(3,5-dimethoxy-4-bromophenyl)-5-(3-hydroxy-4-methoxyphenyl)imidazole (CN11)
4-(3,5-dimethoxy-4-hydroxyphenyl)-5-(3-fluoro-4-methoxyphenyl) imidazole (CN12)
4-(3,5-dimethoxy-4-bromophenyl)-5-(3-amino-4-methoxyphenyl)imidazole (CN13)
4-(3,5-dimethoxy-4-hydroxyphenyl)-5-(3-amino-4-methoxyphenyl)imidazole (CN14)
4-(3,5-dimethoxy-4-hydroxyphenyl)-5-(3-hydroxy-4-methoxyphenyl)imidazole (CN15)
4-(3,5-dimethoxy-4-nitrophenyl)-5-(3-hydroxy-4-methoxyphenyl)imidazole (CN16)
4-(3,5-dimethoxy-4-aminophenyl)-5-(3-hydroxy-4-methoxyphenyl)imidazole (CN17)
4-(3,5-dimethoxy-4-aminophenyl)-5-(3-amino-4-methoxyphenyl) imidazole (CN19)
4-(3,5-dimethoxy-4-fluorophenyl)-5-(3-amino-4-methoxyphenyl)oxazole (CN20)
4-(3,5-dimethoxy-4-chlorophenyl)-5-(3-amino-4-methoxyphenyl)oxazole (CN21)
4-(3,5-dimethoxy-4-trifluoromethoxyphenyl)-5-(3-amino-4-methoxyphenyl)oxazole (CN23)
4-(3,5-dimethoxy-4-methylaminophenyl)-5-(3-amino-4-methoxyphenyl)oxazole (CN24)
4-(3,5-dimethoxy-4-aminophenyl)-5-(3-fluoro-4-methoxyphenyl) imidazole (CN10)
4-(3,5-dimethoxyphenyl)-5-(3-hydroxy-4-methoxyphenyl)oxazole phosphate disodium salt (C110P)
4-(3,5-dimethoxyphenyl)-5-(3-hydroxy-4-methoxyphenyl)oxazole phosphate tromethamine (C110P.tris)
4-(3,5-dimethoxyphenyl)-5-(3-hydroxy-4-methoxyphenyl)imidazole phosphate disodium salt
4-(3,4,5-trimethoxyphenyl)-5-(3-fluoro-4-methoxyphenyl)oxazole (C094)
5-(3,5-dimethoxyphenyl)-4-(3-hydroxy-4-methoxyphenyl)-1-methylimidazole (C126)
4-(3,5-dimethoxyphenyl)-5-(3-hydroxy-4-methoxyphenyl)-1-(3,4,5-trimethoxyphenyl)imidazole (C101).

The pharmaceutically acceptable salts of the present invention are preferably hydrochloride, phosphate, nitrate, sulfate, citrate, maleate, tartrate, sulfonate or amino acid salt.

The pharmaceutically acceptable salts according to the present invention include the salts of the phosphate esters or sulfonate esters of the compounds of formula I, such as alkali metal salts, alkaline-earth metal salts or tromethamine salts. Preferably, said salts are phosphate disodium salts, phosphate tromethamine salts, sulfonate sodium salts, sulfonate disodium salts or sulfonate tromethamine salts of the compounds according to the present invention.

The term "sulfonic acid" used herein (such as sulfonate salt, sulfonate ester) refers to an organic acid with one or more —SO₃H groups, preferably mono-, di-, or tri-sulfonic acid, especially preferably methanesulfonic acid, benzenesulfonic acid, p-toluenesulfonic acid, m-toluenesulfonic acid, o-toluenesulfonic acid, benzene disulfonic acid (o-benzene disulfonic acid, m-benzene disulfonic acid, p-benzene disulfonic acid), naphthalene disulfonic acid, benzene trisulfonic acid, naphthalene trisulfonic acid, and the like.

The present invention further provides the methods for preparing said compounds and pharmaceutically acceptable salts thereof, comprising the following steps:

1) reacting an imine compound with an isonitrile compound in the following scheme in a mixed solvent (such as ethanol and tetrahydrofuran) at a certain temperature (room temperature or reflux) under an alkaline condition (such as potassium carbonate) to get a compound of formula I, and optionally converting it to a pharmaceutically acceptable salt,

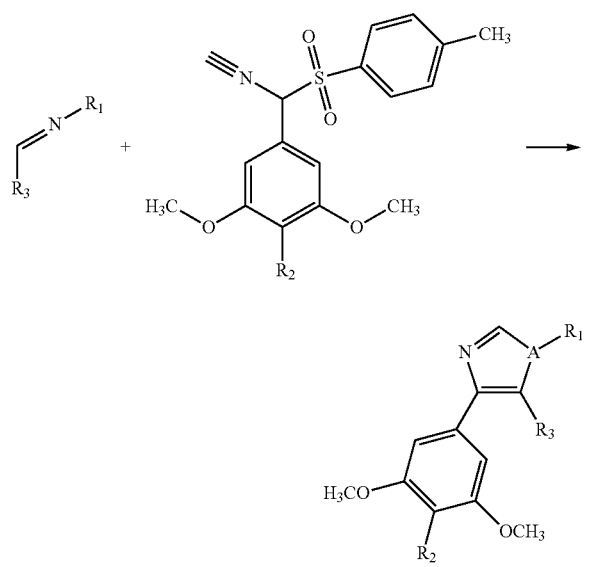

wherein A is N; or 2) reacting an imine compound with an isonitrile compound in the following scheme in a mixed solvent (such as ethanol and tetrahydrofuran) at a certain temperature (room temperature or reflux) under an alkaline condition (such as potassium carbonate or potassium tert-butoxide), and cleaving the benzyl group off from the resultant adduct to get the compound of formula I, wherein A is N, R₁ is H, and optionally converting it to a pharmaceutically acceptable salt,

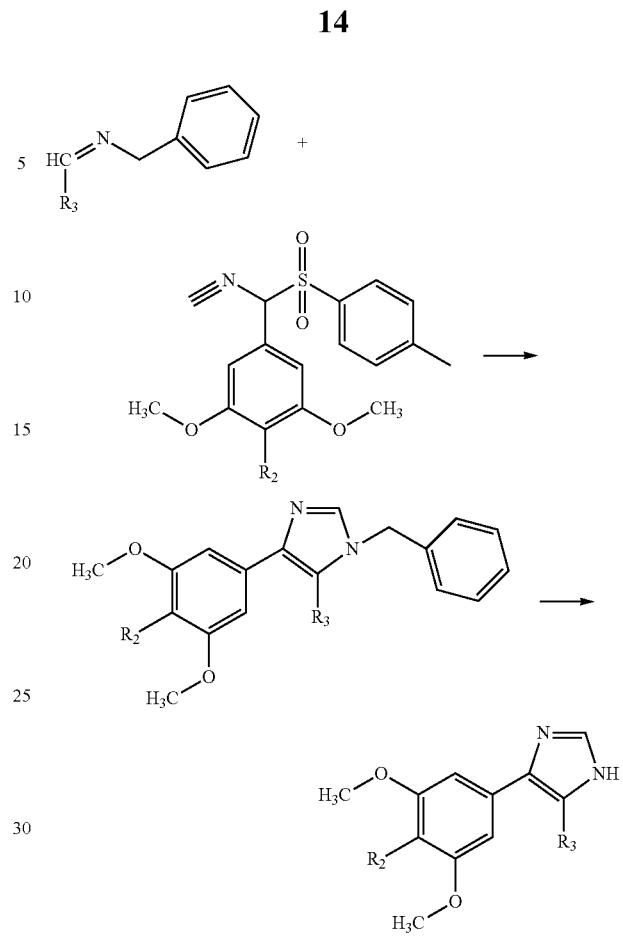

or 3) reacting an aldehyde compound or a sulfaldehyde compound with an isonitrile compound in the following scheme in a mixed solvent (such as ethanol and tetrahydrofuran) at a certain temperature (room temperature or reflux) under an alkaline condition (such as potassium carbonate) to get the compound of formula I, wherein A is O or S, and optionally converting it to a pharmaceutically acceptable salt,

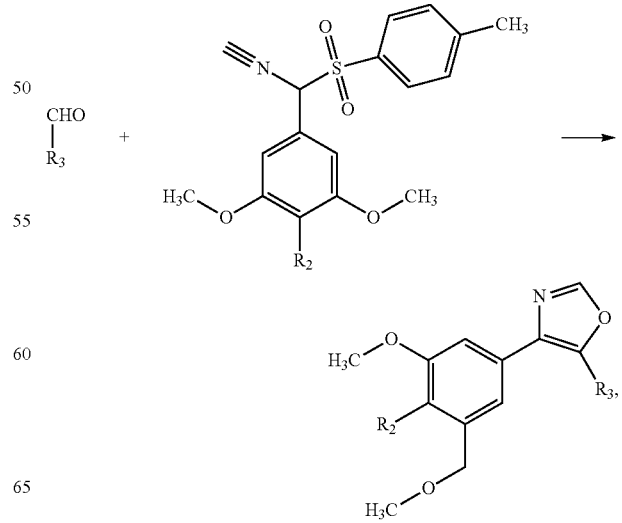

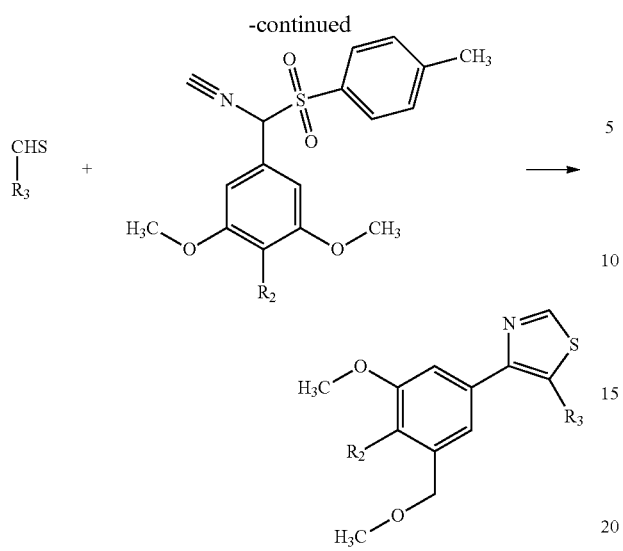

or 4) reacting a compound of formula I comprising one or more hydroxyl groups with a phosphorous acid, di-sulfonic acid, or tri-sulfonic acid to form an ester, and then reacting the resultant ester with an alkaline compound to get a salt. The formation of the salt in process 4) comprises:

a) converting the resultant phosphate ester or sulfonate ester into a salt of alkali metal or alkaline earth metal thereof (such as sodium salt, disodium salt, potassium salt, dipotassium salt, calcium salt, dicalcium salt, etc.); or b) forming a tromethamine salt; or c) optionally converting the salt obtained from step a) or step b) into other salts.

The method of preparing the above-mentioned compounds or pharmaceutically acceptable salts thereof is characterized in that the intermediate compound, obtained from reacting an aldehyde compound with an amide compound at a certain temperature, is reacted with Lawesson's reagent at a certain temperature (e.g. reflux) to give a thiazole compound, which is optionally converted into a pharmaceutically acceptable salt thereof.

Said aldehyde compound is preferably a 6-membered ring, a fused heterocyclic ring, or an aldehyde compound containing a 6-membered ring.

A pharmaceutically acceptable salt of the compounds described above may be prepared by a conventional salt-forming method.

The method of preparing the phosphate disodium salt of the compounds described above is characterized in that the compound and phosphorus oxychloride are reacted with triethylamine in a solvent (e.g., dichloromethane) at a certain temperature (e.g., room temperature) to obtain the phosphate diester, which is then reacted with sodium hydroxide in a solvent (e.g., acetone) at a certain temperature (e.g., room temperature).

The method of preparing the phosphate tromethamine (C110P.tris) of the compounds described aboveis characterized in that the phosphate ester of the compounds of general formula I is reacted with an equimolar amount of tromethamine in a solvent such as isopropanol at a certain temperature (e.g. room temperature).

Optionally, the salt obtained above was converted into other salts.

The present invention provides use of the above-mentioned compounds, or pharmaceutically acceptable salts or prodrugs thereof, in the manufacture of a medicaments for anti-tumor, preferably in the manufacture of medicaments for treating breast cancer, lung cancer, liver cancer, colorectal cancer, gastric cancer, esophageal cancer, pancreatic cancer, prostate cancer or leukemia, more preferably in the manufacture of a medicament for treating breast cancer, lung cancer, liver cancer or leukemia.

The present invention further provides a series of aromatic aldehydes and heterocyclic imines, wherein the imine compounds have the structure of the following formula II:

wherein
R is selected from the group consisting of:

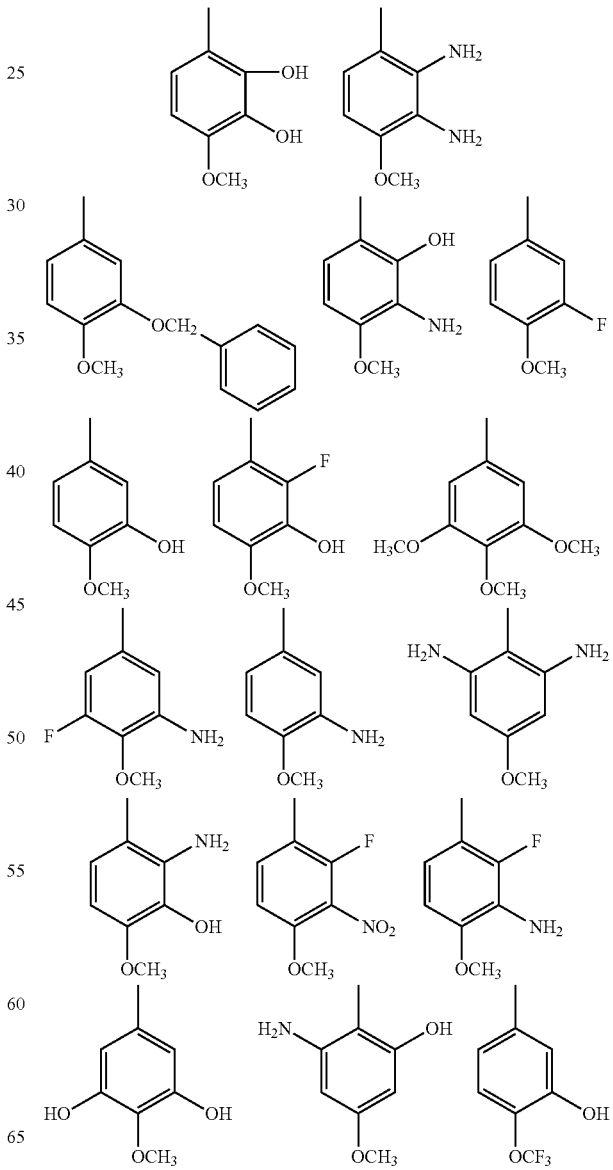

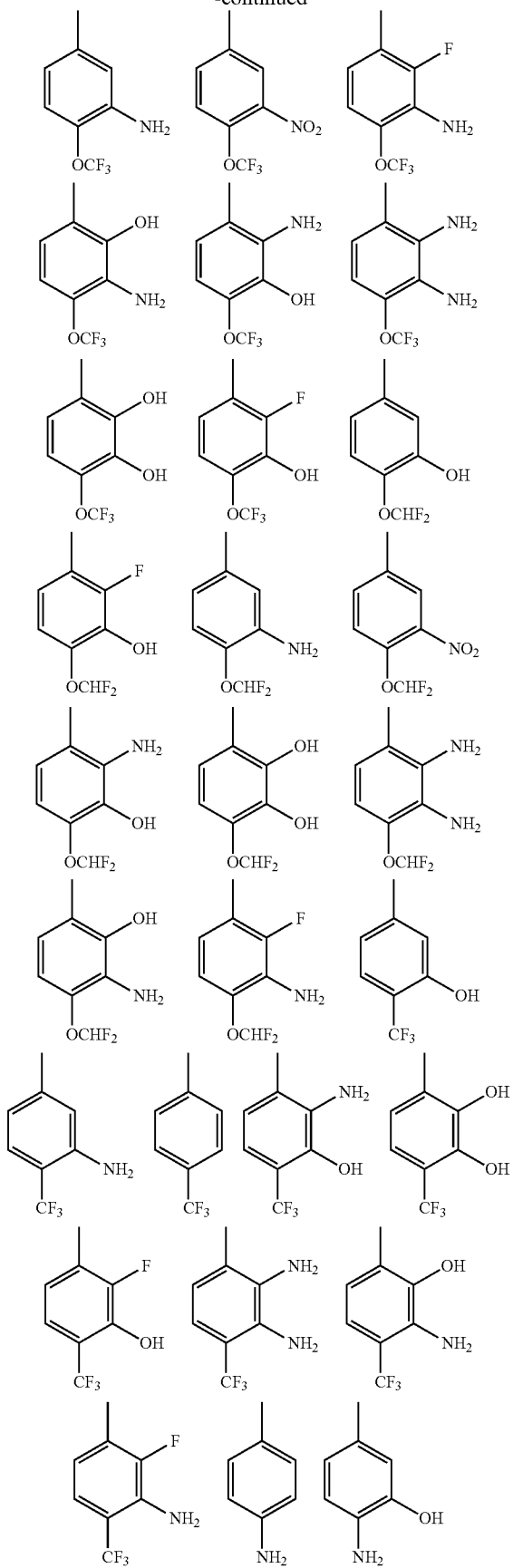
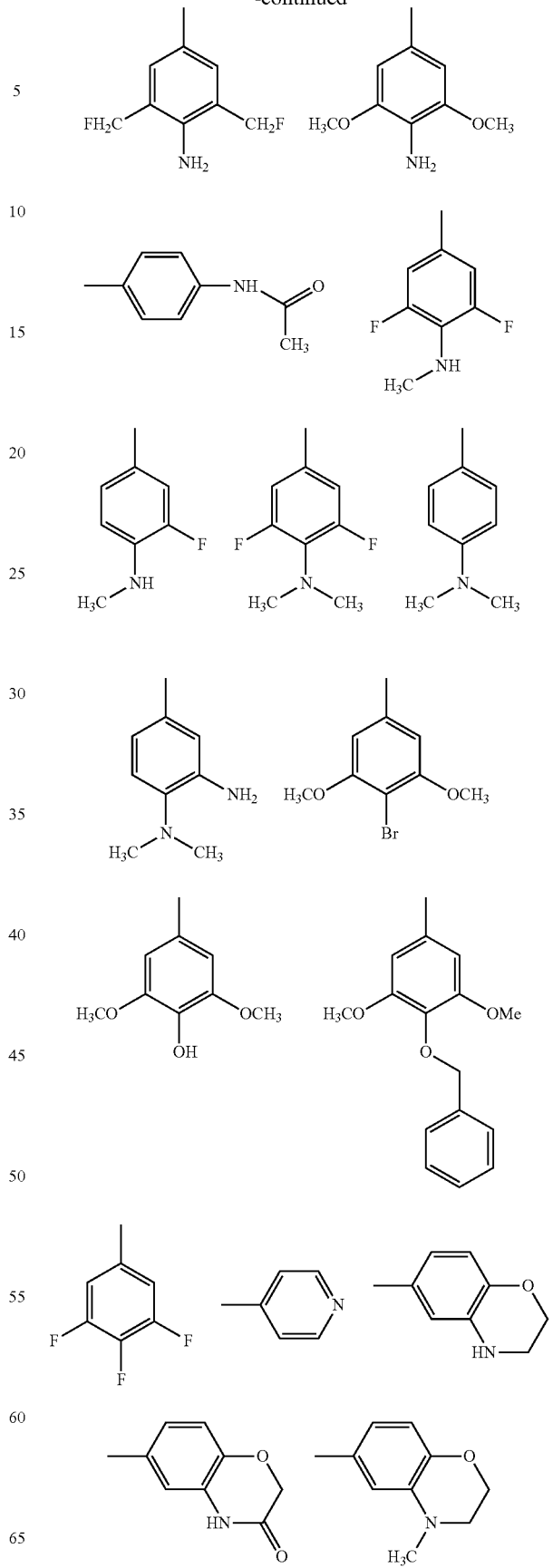

-continued

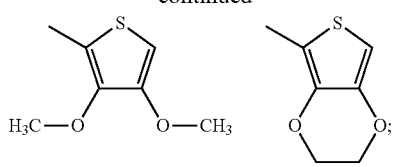

and

R$_1$ is H, CH$_3$, C$_4$H$_9$,

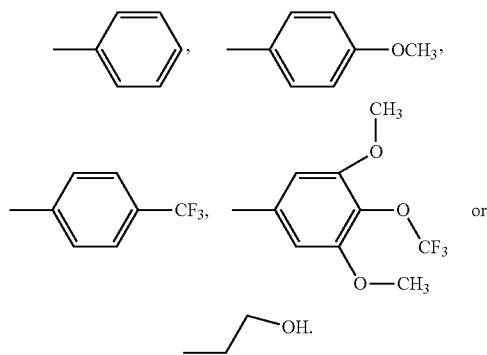

Preferably, the following compounds are excluded:

1) R$_1$ is C$_4$H$_9$, and R is 3,4,5-(OCH$_3$)$_3$—C$_6$H$_2$, 3-F-4-(OCH$_3$)—C$_6$H$_3$, 4-(OCH$_3$)-5-(NH$_2$)—C$_6$H$_3$ or 3-OH-4-(OCH$_3$)—C$_6$H$_3$; and 2) R$_1$ is CH$_3$, and R is 3,4,5-(OCH$_3$)$_3$—C$_6$H$_2$.

In particular, the methods for preparing the compounds according to the present invention comprise:

1. Preparation of the 1-Substituted Imidazole Derivatives

Different 1-substituted imine compounds are respectively reacted with an isonitrile compound in a mixed solvent (e.g., ethanol and tetrahydrofuran) at a certain temperature (reflux) under alkaline conditions, such as potassium carbonate, to give a 1-substituted imidazole derivative. The general reaction scheme is as follows:

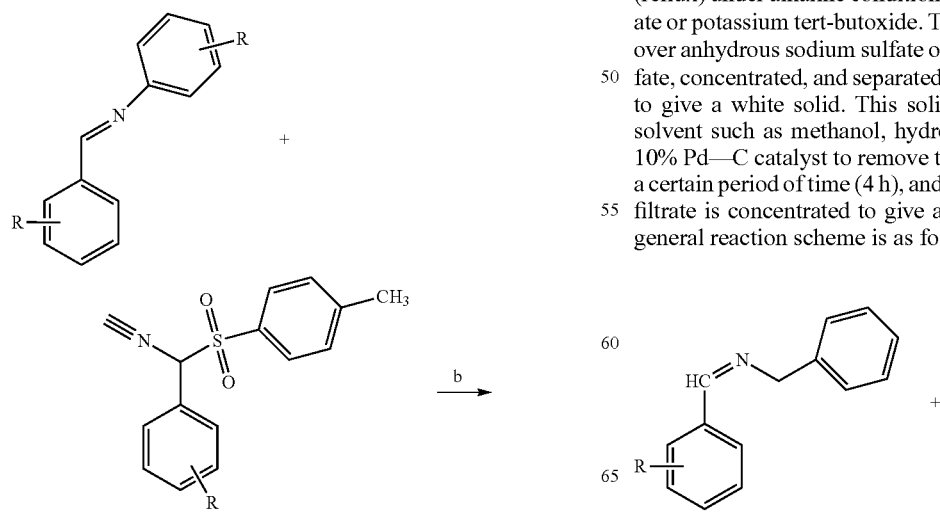

-continued

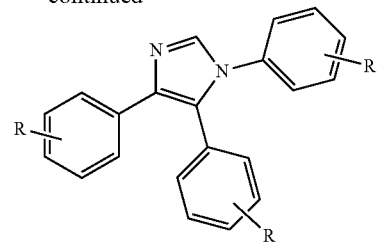

2. Preparation of the Oxazole Derivatives

Different aldehyde compounds are reacted with an isonitrile compound in a mixed solvent (e.g., ethanol and tetrahydrofuran) at a certain temperature under alkaline conditions to give an oxazole derivative. The general reaction scheme is as follows:

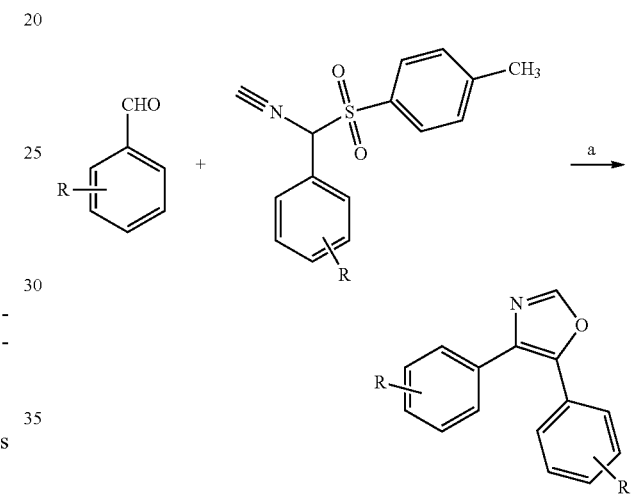

3. Preparation of the Imidazole Derivatives

Benzaldehyde, anhydrous ethanol, benzyl amine and acetic acid are successively introduced into a three-necked flask, dissolved with stirring, and reacted at reflux. The above mixture is reacted with an isonitrile compound in a mixed solvent (e.g., ethanol and tetrahydrofuran) at a certain temperature (reflux) under alkaline conditions, such as potassium carbonate or potassium tert-butoxide. The resulting mixture is dried over anhydrous sodium sulfate or anhydrous magnesium sulfate, concentrated, and separated by column chromatography to give a white solid. This solid is dissolved in a suitable solvent such as methanol, hydrogenated in the presence of 10% Pd—C catalyst to remove the benzyl group, reacted for a certain period of time (4 h), and then filtered by suction. The filtrate is concentrated to give an imidazole derivative. The general reaction scheme is as follows:

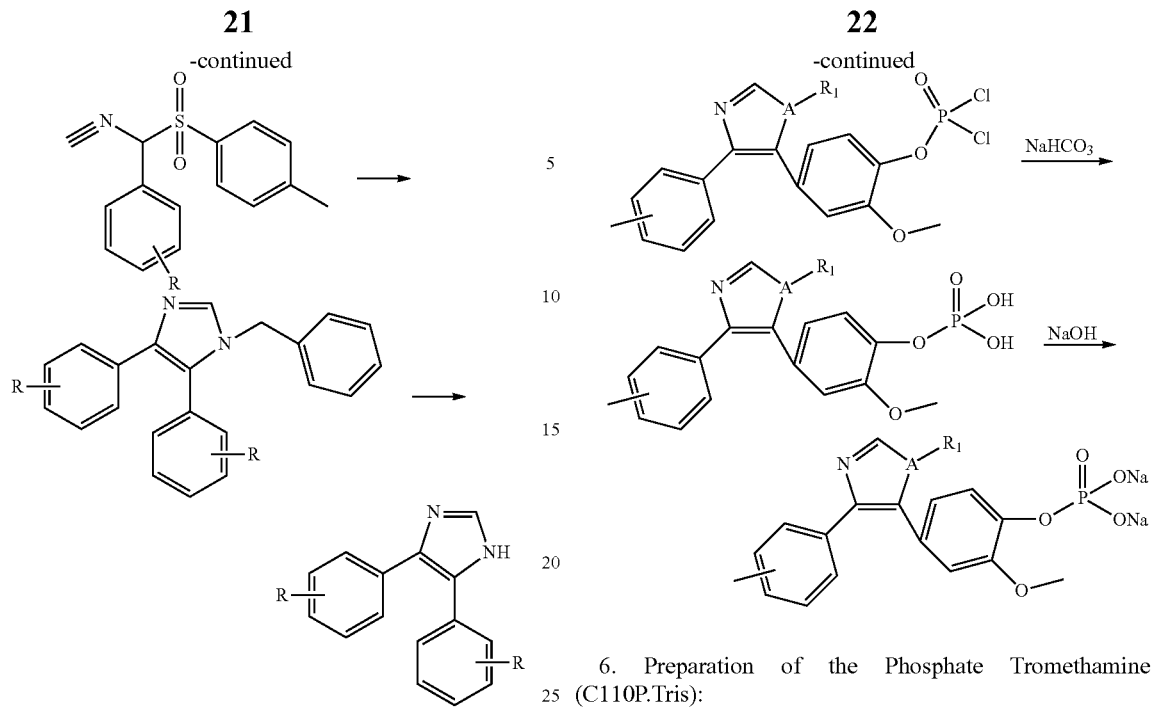

4. Preparation of the Imine Compounds:

For the synthesis of the imines, generally dichloromethane is used as a solvent and anhydrous calcium chloride is used as a water-absorbing agent, and the mixture is stirred at room temperature to obtain the desired intermediate. For the synthesis of an imine compound of methylamine, using anhydrous ethanol as a solvent and a small amount of acetic acid as a catalyst, the reaction is performed under reflux conditions to obtain the imine compound of methylamine. The general reaction scheme is as follows:

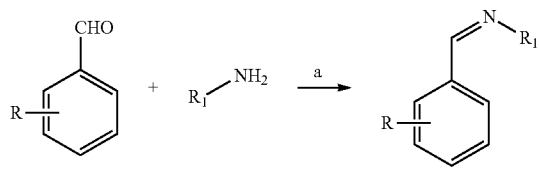

5. Preparation of the Phosphate Disodium Salt:

The compound and phosphorus oxychloride in a solvent (e.g., dichloromethane) are reacted with triethylamine at a certain temperature (e.g., room temperature) to obtain the phosphate diester, which is then reacted with sodium hydroxide in a solvent (e.g., acetone) at a certain temperature (e.g., room temperature). The general reaction scheme is as follows:

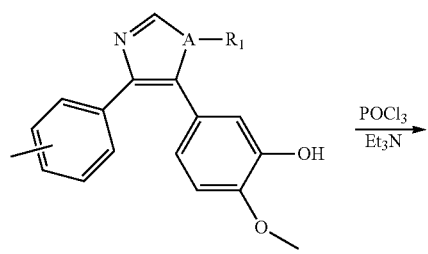

6. Preparation of the Phosphate Tromethamine (C110P.Tris):

The oxazole phosphate is reacted with an equimolar amount of tromethamine in a solvent such as isopropanol at a certain temperature (e.g., room temperature). The general reaction scheme is as follows:

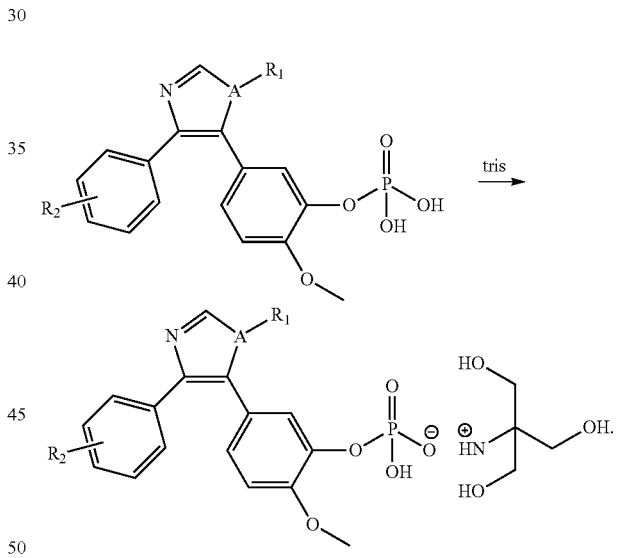

BRIEF DESCRIPTION OF THE DRAWING

FIG. 1 shows the plasma concentration-time curve of compound C128 according to the present invention.

DETAILED DESCRIPTION OF THE INVENTION

Example 1

Preparation of 5-(3-hydroxy-4-methoxyphenyl)-4-(3,5-dimethoxyphenyl)-1-(4-methoxyphenyl)imidazole (C074)

N-4-Methoxyphenyl-3-benzyloxy-4-methoxyphenyl imine (2 mmol), 2 mmol 1-p-toluene sulfonyl-1-(3,5- dimethoxyphenyl) methyl isonitrile, 80 mL anhydrous ethanol, 15 mL tetrahydrofuran and 1.2 mL tert-butylamine were added sequentially into a 250 mL three-necked flask, and the mixture was dissolved with stirring and allowed to react at 25° C. for 6 hours. The solvent was removed under reduced pressure, 50 ml saturated sodium chloride solution was added, and the mixture was extracted with chloroform (30 ml×3). The organic phases were combined, dried over anhydrous sodium sulfate, concentrated and then separated by column chromatography (eluant: ethyl acetate) to give a white solid. This solid was dissolved in methanol and hydrogenated in the presence of 10% Pd—C catalyst to remove benzyl group, and after reacting for 4 hours filtered by suction. The filtrate was concentrated to afford the desired compound, 5-(3-hydroxy-4-methoxyphenyl)-4-(3,5-dimethoxyphenyl)-1-(4-methoxyphenyl)imidazole, as a white solid, melting point: 131~134° C.

$^1$H NMR (CDCl$_3$) δ (ppm): 3.92 (s, 6H, 2×OCH$_3$), 4.07 (s, 3H, 1×OCH$_3$), 4.13 (s, 3H, 1×OCH$_3$), 6.40~6.43 (t, 1H, 1×Ar—H), 6.71~6.81 (m, 7H, 7×Ar—H), 7.1 (m, 2H, 2×Ar—H), 7.67 (s, 1H, imidazole-H).

ESI-MS m/z: 433.2[M+1]$^+$, calculated: 433.2.

Example 2

Preparation of 5-(4-dimethylaminophenyl)-4-(3,5-dimethoxyphenyl)-1-(4-trifluoromethylphenyl)imidazole (C088)

5-(4-dimethylaminophenyl)-4-(3,5-dimethoxyphenyl)-1-(4-trifluoromethylphenyl)imidazole was prepared according to the method as described in Example 1, as a light yellow solid, melting point: 84~84.5° C.

$^1$HNMR (CDCl$_3$) δ (ppm): 3.67 (s, 6H, 2×OCH$_3$), 6.62~6.64 (m, 2H, 2×Ar—H), 7.00~7.03 (m, 2H, 2×Ar—H), 7.24~7.25 (m, 2H, 2×Ar—H), 7.59~7.60 (m, 3H, 3×Ar—H), 7.67~7.68 (m, 2H, 2×Ar—H), 7.78 (s, 1H, imidazole-H).

ESI-MS m/z: 468.2 (M+1)$^+$, calculated: 468.2.

Example 3

Preparation of 5-(3-hydroxy-4-methoxyphenyl)-4-(3,4,5-trimethoxyphenyl)-1-(4-trifluoromethylphenyl)imidazole (C077)

5-(3-Hydroxy-4-methoxyphenyl)-4-(3,4,5-trimethoxyphenyl)-1-(4-trifluoromethylphenyl)imidazole was prepared according to the method as described in Example 1, which is a viscous oil at room temperature.

$^1$HNMR (CDCl$_3$) δ (ppm): 3.86 (s, 6H, 2×OCH$_3$), 3.92 (s, 6H, 2×OCH$_3$), 6.28~6.34 (m, 1H, 1×Ar—H), 6.69~6.85 (m, 4H, 4×Ar—H), 7.10 (d, 2H, 2×Ar—H), 7.20~7.25 (d, 2H, 2×Ar—H), 7.89 (s, 1H, imidazole-H).

ESI-MS m/z: 501.2 [M+H]$^+$, calculated: 501.1.

Example 4

Preparation of 5-(3-hydroxy-4-methoxyphenyl)-4-(3,4,5-trimethoxyphenyl)-1-phenylimidazole (C087)

5-(3-Hydroxy-4-methoxyphenyl)-4-(3,4,5-trimethoxyphenyl)-1-phenylimidazole was prepared according to the method as described in Example 1, as a white solid, melting point: 176-177° C.

$^1$HNMR (CDCl$_3$) δ (ppm): 3.66 (s, 6H, 2×OCH$_3$), 3.84 (s, 3H, 1×OCH$_3$), 3.86 (s, 3H, 1×OCH$_3$), 6.72 (s, 1H, 1×Ar—H), 6.80~6.82 (m, 4H, 4×Ar—H), 7.05~7.07 (m, 2H, 2×Ar—H), 7.27~7.31 (m, 3H, 3×Ar—H), 7.72 (s, 1H, imidazole-H).

ESI-MS m/z: 433.2 [M+1]$^+$, calculated: 433.1.

Example 5

Preparation of 5-(3-hydroxy-4-methoxyphenyl)-4-(3,5-dimethoxyphenyl)-1-(4-trifluoromethylphenyl)imidazole (C081)

5-(3-Hydroxy-4-methoxyphenyl)-4-(3,5-dimethoxyphenyl)-1-(4-trifluoromethylphenyl)imidazole was prepared according to the methods as described above, as a light yellow solid, melting point: 111~113° C.

$^1$HNMR (CDCl$_3$) δ (ppm): 3.72 (s, 6H, 2×OCH$_3$), 3.93 (s, 3H, 1×OCH$_3$), 6.34~6.35 (t, 1H, 1×Ar—H), 6.74~6.88 (m, 5H, 5×Ar—H), 7.11 (d, 2H, 2×Ar—H), 7.64 (d, 2H, 2×Ar—H), 7.88 (s, 1H, imidazole-H).

ESI-MS m/z: 471.2[M+H]$^+$, calculated: 471.1.

Example 6

Preparation of 5-(3-hydroxy-4-methoxyphenyl)-4-(3,4,5-trimethoxyphenyl)-1-(4-methoxyphenyl)imidazole (C075)

5-(3-Hydroxy-4-methoxyphenyl)-4-(3,4,5-trimethoxyphenyl)-1-(4-methoxyphenyl)imidazole was prepared according to the method as described in Example 1, as a white solid, melting point: 65~67° C.

$^1$HNMR (CDCl$_3$) δ (ppm): 3.83 (s, 6H, 2×OCH$_3$), 3.94 (s, 3H, 1×OCH$_3$), 4.06 (s, 3H, 1×OCH$_3$), 4.12 (s, 3H, 1×OCH$_3$), 6.72~6.86 (m, 7H, 7×Ar—H), 7.11 (m, 2H, 2×Ar—H), 7.86 (s, 1H, imidazole-H).

ESI-MS m/z: 463.2[M+1]$^+$, calculated: 463.2.

Example 7

Preparation of 5-(3-fluoro-4-methoxyphenyl)-4-(3,5-dimethoxyphenyl)-1-(3,4,5-trimethoxyphenyl)imidazole (C091)

5-(3-Fluoro-4-methoxyphenyl)-4-(3,5-dimethoxyphenyl)-1-(3,4,5-trimethoxyphenyl)imidazole was prepared according to the method as described in Example 1, as a white solid, melting point: 157-158.4° C.

$^1$HNMR (CDCl$_3$) δ (ppm): 3.72 (s, 12H, 4×OCH$_3$), 3.85 (s, 3H, 1×OCH$_3$), 3.89 (s, 3H, 1×OCH$_3$), 6.33 (s, 2H, 2×Ar—H), 6.36~6.37 (d, 1H, 1×Ar—H), 6.74~6.76 (d, 2H, 2×Ar—H), 6.89~6.92 (m, 2H, 2×Ar—H), 6.95~6.97 (m, 1H, Ar—H), 7.76 (s, 1H, imidazole-H).

ESI-MS m/z: 495.2 (M+1)$^+$, calculated: 495.2.

Example 8

Preparation of 5-(4-dimethylaminophenyl)-4-(3,4,5-trimethoxyphenyl)-1-(4-trifluoromethylphenyl)imidazole (C092)

5-(4-Dimethylaminophenyl)-4-(3,4,5-trimethoxyphenyl)-1-(4-trifluoromethylphenyl)imidazole was prepared according to the method as described in Example 1, as a light yellow solid, melting point: 215-217° C.

$^1$HNMR (CDCl$_3$) δ (ppm): 2.96 (s, 6H, 2×N—CH$_3$), 3.70 (s, 6H, 2×OCH$_3$), 3.84 (s, 3H, 1×OCH$_3$), 6.64~6.66 (d, 2H, 2×Ar—H), 6.93 (s, 2H, 2×Ar—H), 7.02~7.04 (m, 2H, 2×Ar—H), 7.30~7.32 (m, 2H, 2×Ar—H), 7.65~7.67 (m, 2H, 2×Ar—H), 8.10 (s, 1H, imidazole-H).
ESI-MS m/z: 498.3 (M+1)$^+$, calculated: 498.2.

Example 9

Preparation of 5-(3,4,5-trimethoxyphenyl)-4-(3,5-dimethoxyphenyl)-1-(4-trifluoromethylphenyl)imidazole (C093)

5-(3,4,5-Trimethoxyphenyl)-4-(3,5-dimethoxyphenyl)-1-(4-trifluoromethylphenyl)imidazole was prepared according to the method as described in Example 1, as a viscous liquid.
$^1$HNMR (CDCl$_3$) δ (ppm): 3.60 (s, 6H, 2×OCH$_3$), 3.68 (s, 6H, 2×OCH$_3$), 3.85 (m, 3H, 1×OCH$_3$), 6.35~6.37 (m, 2H, 2×Ar—H), 6.78~6.79 (d, 2H, 2×Ar—H), 6.88 (m, 1H, 1×Ar—H), 7.28~7.30 (m, 2H, 2×Ar—H), 7.64~7.65 (m, 2H, 2×Ar—H), 7.82 (s, 1H, imidazole-H).
ESI-MS m/z: 515.2 (M+1)$^+$, calculated: 515.2.

Example 10

Preparation of 5-(4-dimethylaminophenyl)-4-(3,5-dimethoxyphenyl)-1-(3,4,5-trimethoxyphenyl)imidazole (C098)

5-(4-Dimethylaminophenyl)-4-(3,5-dimethoxyphenyl)-1-(3,4,5-trimethoxyphenyl)imidazole was prepared according to the method as described in Example 1, as a light yellow solid, melting point: 151~154° C.
$^1$HNMR (CDCl$_3$) δ (ppm): 2.93 (s, 6H, 2×N—CH$_3$), 3.64~3.70 (m, 12H, 4×OCH$_3$), 3.87 (s, 3H, 1×OCH$_3$), 6.31~6.33 (m, 2H, 2×Ar—H), 6.37~6.39 (m, 1H, 1×Ar—H), 6.62~6.64 (m, 2H, 2×Ar—H), 6.82~6.84 (m, 2H, 2×Ar—H), 7.04~7.06 (m, 2H, 2×Ar—H), 7.75 (s, 1H, imidazole-H).
ESI-MS m/z: 490.3 (M+1)$^+$, calculated: 490.2.

Example 11

Preparation of 5-(3,4,5-trimethoxyphenyl)-4-(3,4-dimethoxyphenyl)-1-(3,4,5-trimethoxyphenyl)imidazole (C104)

5-(3,4,5-Trimethoxyphenyl)-4-(3,4-dimethoxyphenyl)-1-(3,4,5-trimethoxyphenyl)imidazole was prepared according to the method as described in Example 1, as a white solid, melting point: 159.5-161° C.
$^1$HNMR (CDCl$_3$) δ (ppm): 3.63 (s, 6H, 2×OCH$_3$), 3.69~3.70 (s, 12H, 4×OCH$_3$), 3.84 (s, 6H, 2×OCH$_3$), 6.35~6.36 (t, 1H, 1×Ar—H), 6.37 (s, 2H, 2×Ar—H), 6.43 (s, 2H, 2×Ar—H), 6.82~6.83 (d, 2H, 2×Ar—H), 7.78 (s, 1H, imidazole-H).
ESI-MS m/z: 537.3 (M+1)$^+$, calculated: 537.2.

Example 12

Preparation of 5-(4-dimethylaminophenyl)-4-(3,4,5-trimethoxyphenyl)-1-(3,4,5-trimethoxyphenyl)imidazole (C106)

5-(4-Dimethylaminophenyl)-4-(3,4,5-trimethoxyphenyl)-1-(3,4,5-trimethoxyphenyl)imidazole was prepared according to the method as described in Example 1, as a white solid, melting point: 168.8-170.9° C.
$^1$HNMR (CDCl$_3$) δ (ppm): 2.93 (s, 6H, 2×N—CH$_3$), 3.68 (s, 6H, 2×OCH$_3$), 3.69 (s, 6H, 2×OCH$_3$), 3.83 (s, 6H, 2×OCH$_3$), 6.35 (d, 2H, 2×Ar—H), 6.64~6.66 (d, 2H, 2×Ar—H), 6.89 (s, 2H, 2×Ar—H), 7.06~7.08 (d, 2H, 2×Ar—H), 7.76 (s, 1H, imidazole-H).
ESI-MS m/z: 520.3 (M+1)$^+$, calculated: 520.2.

Example 13

Preparation of 5-(3-hydroxy-4-methoxyphenyl)-4-(3,4,5-trimethoxyphenyl)-1-(3,4,5-trimethoxyphenyl)imidazole (C105)

5-(3-Hydroxy-4-methoxyphenyl)-4-(3,4,5-trimethoxyphenyl)-1-(3,4,5-trimethoxyphenyl)imidazole was prepared according to the method as described in Example 1, as a white solid, melting point: 154~156° C.
$^1$HNMR (CDCl3) δ (ppm): 3.67 (s, 12H, 4×OCH$_3$), 3.84 (s, 6H, 2×OCH$_3$), 3.87 (s, 3H, 1×OCH$_3$), 6.29 (s, 2H, 2×Ar—H), 6.77 (s, 1H, 1×Ar—H), 6.81~6.83 (m, 3H, 3×Ar—H), 6.82~6.86 (m, 1H, 1×Ar—H), 7.74 (s, 1H, imidazole-H).
ESI-MS m/z: 523.2 (M+1)$^+$, calculated: 523.2.

Example 14

Preparation of 5-(3,4,5-trimethoxyphenyl)-4-(3,4,5-trimethoxyphenyl)-1-(3,4,5-trimethoxyphenyl)imidazole (C107)

5-(3,4,5-Trimethoxyphenyl)-4-(3,4,5-trimethoxyphenyl)-1-(3,4,5-trimethoxyphenyl)imidazole was prepared according to the method as described in Example 1, as a white solid, melting point: 168.8-170.9° C.
$^1$HNMR (CDCl$_3$) δ (ppm): 3.65 (s, 6H, 2×OCH$_3$), 3.70 (s, 6H, 2×OCH$_3$), 3.71 (s, 6H, 2×OCH$_3$), 3.82 (s, 3H, OCH$_3$), 3.84 (s, 6H, 2×OCH$_3$), 6.38 (d, 2H, 2×Ar—H), 6.46 (d, 2H, 2×Ar—H), 6.89 (s, 2H, 2×Ar—H), 7.79 (s, 1H, imidazole-H).
ESI-MS m/z: 567.3 (M+1)$^+$, calculated: 567.2.

Example 15

Preparation of 5-(4-acetamidophenyl)-4-(3,5-dimethoxyphenyl)oxazole (C109)

Benzaldehyde, isonitrile, anhydrous ethanol, tetrahydrofuran and potassium carbonate were successively added into a three-necked flask, and dissolved with stirring, and reacted at reflux. After the complete reaction, ethanol was evaporated under reduced pressure. The residue was purified by silica gel column chromatography to give yellow needle crystals, i.e., 5-(4-aminophenyl acetate)-4-(3,5-dimethoxyphenyl)oxazole, melting point 140.1-143.2.
$^1$HNMR (CDCl$_3$) δ (ppm): 2.20 (s, 3H, 1×CH$_3$), 3.76 (s, 6H, 2×OCH$_3$), 6.45~6.46 (m, 1H, 1×N—H), 6.81~6.82 (d, 2H, 2×Ar—H), 7.17 (d, 1H, 1×Ar—H), 7.55 (d, 2H, 2×Ar—H), 7.59~7.61 (d, 2H, 2×Ar—H), 7.92 (s, 1H, oxazole-H).
ESI-MS m/z: 339.3, calculated: 339.1.

Example 16

Preparation of 4-(3,5-dimethoxyphenyl)-5-(3-hydroxy-4-methoxyphenyl)oxazole (C110)

4-(3,5-Dimethoxyphenyl)-5-(3-hydroxy-4-methoxyphenyl)oxazole was prepared according to the method as described in Example 15, a khaki solid, melting point: 149.9-151.6.
$^1$HNMR (CDCl$_3$) δ (ppm): 3.92 (s, 3H, 1×OCH$_3$), 3.96 (s, 6H, 2×OCH$_3$), 6.26 (m, 1H, 1×Ar—H), 6.71~6.75 (d, 2H, 2×Ar—H), 6.81~6.85 (m, 1H, 1×Ar—H), 7.27~7.28 (m, 2H, Ar—H), 7.70 (s, 1H, oxazole-H).

ESI-MS m/z: 328.2 [M+1]$^+$, calculated: 328.1.

Example 17

Preparation of 4-(3,5-dimethoxyphenyl)-5-(4-aminophenyl)oxazole (C112)

4-(3,5-Dimethoxyphenyl)-5-(4-aminophenyl)oxazole was prepared according to the method as described in Example 15, as an off-white solid, melting point: 142-146° C.

$^1$HNMR (CDCl$_3$) δ (ppm): 3.88 (s, 6H, 2×OCH$_3$), 6.80~6.91 (d, 2H, 2×Ar—H), 7.65 (d, 1H, 1×Ar—H), 7.79 (d, 2H, 2×Ar—H), 7.92~7.99 (d, 2H, 2×Ar—H), 8.14 (s, 1H, oxazole-H).

ESI-MS m/z: 297.5 [M+1]$^+$, calculated: 297.2.

Example 18

Preparation of 4-(3,5-dimethoxyphenyl)-5-(3-amino-4-dimethylaminophenyl)oxazole (C113)

4-(3,5-Dimethoxyphenyl)-5-(3-amino-4-dimethylaminophenyl)oxazole was prepared according to the method as described in Example 15, as a yellow solid, melting point: 111.7-113.5.

$^1$HNMR (CDCl$_3$) δ (ppm): 2.71 (s, 6H, 2×N—CH$_3$), 3.76 (s, 6H, 2×OCH$_3$), 3.98 (broad, 2H, 1×N—H$_2$), 6.43~6.44 (t, 1H, 1×Ar—H), 6.86~6.87 (d, 2H, 2×Ar—H), 6.98~7.00 (d, 3H, 3×Ar—H), 7.88 (s, H, oxazole-H).

ESI-MS m/z: 340.3 [M+1]$^+$, calculated: 340.2

Example 19

Preparation of 4-(3,5-dimethoxyphenyl)-5-(3-amino-4-methoxy-5-fluorophenyl)oxazole (C114)

4-(3,5-Dimethoxyphenyl)-5-(3-amino-4-methoxy-5-fluorophenyl)oxazole was prepared according to the method as described in Example 15, which is a yellowish brown oil at room temperature.

$^1$HNMR (CDCl$_3$) δ (ppm): 3.79 (s, 6H, 2×OCH$_3$), 4.10 (s, 3H, 1×OCH$_3$), 6.51~6.52 (m, 1H, 1×Ar—H), 6.76~6.77 (m, 2H, 2×Ar—H), 7.59~7.62 (m, 1H, 1×Ar—H), 7.88~7.89 (m, 1H, 1×Ar—H), 7.96 (s, H, oxazole-H).

ESI-MS m/z: 345.2[M+1]$^+$, calculated: 345.1.

Example 20

Preparation of 4-(3,5-dimethoxyphenyl)-5-(3-amino-4-methoxyphenyl)oxazole (C115)

4-(3,5-Dimethoxyphenyl)-5-(3-amino-4-methoxyphenyl)oxazole was prepared according to the method as described in Example 15, as a white solid, melting point: 163~165.4° C.

$^1$HNMR (CDCl$_3$) δ (ppm): 3.56 (s, 6H, 2×OCH$_3$), 4.16 (s, 3H, 1×OCH$_3$), 5.62~5.95 (m, 2H, 1×N—H$_2$), 6.42~6.59 (d, 2H, 2×Ar—H), 7.37 (d, 2H, 2×Ar—H), 7.62~7.71 (d, 2H, 2×Ar—H), 7.74 (s, 1H, oxazole-H).

ESI-MS m/z: 327.3[M+1]$^+$, Calculated: 327.1.

Example 21

Preparation of 4-(3,5-dimethoxyphenyl)-5-(2,3-dihydroxy-4-methoxyphenyl)oxazole (C116)

4-(3,5-Dimethoxyphenyl)-5-(2,3-dihydroxy-4-methoxyphenyl)oxazole was prepared according to the method as described in Example 15, as a white solid, melting point: 178.6-180.4.

$^1$HNMR (CDCl$_3$) δ (ppm): 3.71 (s, 6H, 2×OCH$_3$), 3.93 (s, 3H, 1×OCH$_3$), 6.38~6.39 (t, 1H, 1×Ar—H), 6.55~6.57 (d, 1H, 1×Ar—H), 6.82~6.83 (d, 2H, 2×Ar—H), 6.92~6.94 (d, 1H, 1×Ar—H), 7.96 (s, H, oxazole-H).

ESI-MS m/z: 344.2 [M+1]$^+$, calculated: 344.1.

Example 22

Preparation of 4-(3,5-dimethoxyphenyl)-5-(2-fluoro-3-hydroxy-4-methoxyphenyl)oxazole (C117)

4-(3,5-Dimethoxyphenyl)-5-(2-fluoro-3-hydroxy-4-methoxyphenyl)oxazole was prepared according to the method as described in Example 15, as a white solid, melting point: 168.1-172.4° C.

$^1$HNMR (CDCl$_3$) δ (ppm): 3.73 (m, 6H, 2×OCH$_3$), 3.96 (s, 3H, 1×OCH$_3$), 6.40~6.41 (m, 1H, 1×Ar—H), 6.72~6.74 (m, 1H, 1×Ar—H), 6.79~6.80 (d, 2H, 2×Ar—H), 6.96~6.99 (m, 1H, 1×Ar—H), 7.98 (s, H, oxazole-H).

ESI-MS m/z: 346.2[M+1]$^+$, calculated: 346.1.

Example 23

Preparation of 4-(3,5-dimethoxyphenyl)-5-(2,5-diamino-4-methoxyphenyl)oxazole (C119)

4-(3,5-Dimethoxyphenyl)-5-(2,5-diamino-4-methoxyphenyl)oxazole was prepared according to the method as described in Example 15, as a white solid, melting point: 149.9-151.6° C.

$^1$HNMR (CDCl$_3$) δ (ppm): 3.56 (m, 6H, 2×OCH$_3$), 4.16 (s, 3H, 1×OCH$_3$), 6.36~6.47 (m, 1H, 1×Ar—H), 6.52~6.61 (m, 1H, 1×Ar—H), 6.89~6.92 (m, 2H, 2×Ar—H), 6.99~7.15 (m, 1H, 1×Ar—H), 8.12 (s, H, oxazole-H).

ESI-MS m/z: 342.3 [M+1]$^+$, calculated: 342.1.

Example 24

Preparation of 4-(3,5-dimethoxyphenyl)-5-(2,3-diamino-4-methoxyphenyl)oxazole (C121)

4-(3,5-Dimethoxyphenyl)-5-(2,3-diamino-4-methoxyphenyl)oxazole was prepared according to the method as described in Example 15, as a white solid, melting point: 132.6-134.0° C.

$^1$HNMR (CDCl$_3$) δ (ppm): 3.95 (m, 6H, 2×OCH$_3$), 4.12 (s, 3H, 1×OCH$_3$), 6.39 (m, 1H, 1×Ar—H), 6.54~6.57 (m, 1H, 1×Ar—H), 6.82~6.94 (m, 2H, 2×Ar—H), 7.26 (m, 1H, 1×Ar—H), 7.97 (s, H, oxazole-H).

ESI-MS m/z: 342.1[M+1]$^+$, calculated: 342.1.

Example 25

Preparation of 4-(3,5-dimethoxyphenyl)-5-(3-hydroxy-4-methylaminophenyl)oxazole (C123)

4-(3,5-Dimethoxyphenyl)-5-(3-hydroxy-4-methylaminophenyl)oxazole was prepared according to the method as described in Example 15, as a white solid, melting point: 149.9-151.6° C.

$^1$HNMR (CDCl$_3$) δ (ppm): 3.37~3.41 (s, 3H, 1×N—CH$_3$), 3.70~3.81 (m, 6H, 2×OCH$_3$), 6.46 (s, 1H, 1×Ar—H), 6.78~6.79 (m, 2H, 2×Ar—H), 6.94~6.97 (m, 1H, 1×Ar—H), 7.47~7.50 (m, 2H, 2×Ar—H), 7.95 (s, H, oxazole-H).

ESI-MS m/z: 327.2 [M+1]$^+$, calculated: 327.1.

Example 26

Preparation of 4-(3,5-dimethoxyphenyl)-5-(2-amino-3-hydroxy-4-methoxyphenyl)oxazole (C124)

4-(3,5-Dimethoxyphenyl)-5-(2-amino-3-hydroxy-4-methoxyphenyl)oxazole was prepared according to the method as described in Example 15, as a white solid, melting point: 139.8~142.7° C.

$^1$HNMR (CDCl$_3$) δ (ppm): 3.69~3.77 (m, 6H, 2×OCH$_3$), 3.91 (s, 3H, 1×OCH$_3$), 6.32~6.47 (m, 2H, 2×Ar—H), 6.78~6.84 (m, 1H, 1×Ar—H), 7.06~7.15 (m, 1H, 1×Ar—H), 7.20~7.26 (m, 1H, 1×Ar—H), 7.89 (s, H, oxazole-H).

ESI-MS m/z: 343.2 [M+1]$^+$, calculated: 343.1.

Example 27

Preparation of 4-(3,5-dimethoxyphenyl)-5-(3-amino-4-trifluoromethoxyphenyl)oxazole (C131)

4-(3,5-Dimethoxyphenyl)-5-(3-amino-4-trifluoromethoxyphenyl)oxazole was prepared according to the method as described in Example 15, as a yellow solid, melting point: 119.2~120.3° C.

$^1$HNMR (CDCl$_3$) δ (ppm): 3.72~3.77 (m, 6H, 2×OCH$_3$), 6.45~6.46 (m, 1H, 1×Ar—H), 6.81~6.85 (m, 1H, 1×Ar—H), 6.91~6.96 (m, 1H, 1×Ar—H), 7.11~7.13 (m, 1H, 1×Ar—H), 7.26 (m, 1H, 1×Ar—H), 7.30~7.31 (m, 1H, 1×Ar—H), 7.92 (s, H, oxazole-H).

ESI-MS m/z: 381.2[M+1]$^+$, calculated: 381.1.

Example 28

Preparation of 4-(3,5-dimethoxyphenyl)-5-(3-amino-4-difluoromethoxyphenyl)oxazole (C133)

4-(3,5-Dimethoxyphenyl)-5-(3-amino-4-difluoromethoxyphenyl)oxazole was prepared according to the method as described in Example 15, as a yellow solid, melting point: 104.7~105.1° C.

$^1$HNMR (CDCl$_3$) δ (ppm): 3.75~3.77 (m, 6H, 2×OCH$_3$), 4.06 (s, 1H, 1×OCF$_2$H), 6.44~6.45 (m, 1H, 1×Ar—H), 6.78~6.80 (m, 2H, 2×Ar—H), 7.59~7.60 (m, 2H, 2×Ar—H), 6.95~7.07 (m, 2H, 2×Ar—H), 7.82~7.83 (m, 1H, 1×Ar—H), 8.41 (s, 1H, oxazole-H).

ESI-MS m/z: 363.2[M+1]$^+$, calculated: 363.1.

Example 29

Preparation of 4-(3,5-dimethoxyphenyl)-5-(2-hydroxy-4-methoxy-5-aminophenyl)oxazole (C137)

4-(3,5-Dimethoxyphenyl)-5-(2-hydroxy-4-methoxy-5-aminophenyl)oxazole was prepared according to the method as described in Example 15, as a yellow solid, melting point: 122.2~122.8° C.

$^1$HNMR (CDCl$_3$) δ (ppm): 3.66 (m, 6H, 2×OCH$_3$), 3.77 (s, 3H, 1×OCH$_3$), 6.28~6.29 (m, 1H, 1×Ar—H), 6.42~6.53 (m, 2H, 2×Ar—H), 6.75~6.76 (m, 2H, 2×Ar—H), 8.06 (s, 1H, oxazole-H).

ESI-MS m/z: 343.2[M+1]$^+$, calculated: 343.1.

Example 30

Preparation of 4-(3,5-dimethoxyphenyl)-5-(3-amino-4-trifluoromethoxyphenyl)-1-methylimidazole (C132)

3-Amino-4-trifluoromethoxy benzaldehyde, 20 mL anhydrous ethanol and 5 mL methylamine alcohol solution were sequentially added into a three-necked flask, dissolved with stirring, and reacted at reflux. Subsequently, potassium carbonate, N-(3,5-dimethoxyphenyl)-1-p-toluenesulfonyl methyl isonitrile and tetrahydrofuran were successively added. The mixture was reacted at 50° C. with stirring. After cooling, the ethanol was evaporated under reduced pressure. The residue was purified by silica gel column chromatography to give 4-(3,5-dimethoxyphenyl)-5-(3-amino-4-trifluoromethoxyphenyl)-1-methylimidazole, as a yellow solid, melting point: 112.0~113.8° C.

$^1$HNMR (CDCl$_3$) δ (ppm): 2.86 (s, 3H, NCH$_3$), 3.66 (s, 6H, 2×OCH$_3$), 6.26~6.29 (m, 1H, 1×Ar—H), 6.60~6.61 (s, 1H, 1×Ar—H), 6.65~6.67 (m, 1H, 1×Ar—H), 6.76~6.77 (d, 1H, 1×Ar—H), 6.79~6.80 (m, 2H, 2×Ar—H), 7.48 (s, 1H, imidazole-H).

ESI-MS m/z: 394.1[M+1]$^+$, calculated: 394.1.

Example 31

Preparation of 4-(3,5-dimethoxyphenyl)-5-(3-amino-4-difluoromethoxyphenyl)-1-methylimidazole (C135)

4-(3,5-Dimethoxyphenyl)-5-(3-amino-4-difluoromethoxyphenyl)-1-methylimidazole was prepared according to the method as described in Example 30, as a yellow solid, melting point: 99.2-101.3° C.

$^1$HNMR (CDCl$_3$) δ (ppm): 2.95~2.97 (s, 3H, 1×CH$_3$), 3.81~3.84 (m, 6H, 2×OCH$_3$), 4.09 (s, 1H, OCHF$_2$), 6.45~6.46 (m, 1H, 1×Ar—H), 6.65 (m, 1H, 1×Ar—H), 6.72~6.73 (d, 1H, 1×Ar—H), 7.20~7.21 (m, 1H, 1×Ar—H), 7.34~7.55 (m, 2H, 2×Ar—H), 8.04 (s, 1H, imidazole-H).

ESI-MS m/z: 376.4[M+1]$^+$, calculated 376.1.

Example 32

Preparation of 4-(3,5-dimethoxyphenyl)-5-(2-fluoro-3-amino-4-methoxyphenyl)-1-methylimidazole (C136)

4-(3,5-Dimethoxyphenyl)-5-(2-fluoro-3-amino-4-methoxyphenyl)-1-methylimidazole was prepared according to the method as described in Example 30, as a yellow solid, melting point: 124.9~126.1° C.

¹HNMR (CDCl₃) δ (ppm): 3.08~3.09 (s, 3H, 1×CH₃), 3.52 (m, 3H, 1×OCH₃), 3.70 (s, 6H, 2×OCH₃), 6.31~6.32 (m, 1H, 1×Ar—H), 6.71~6.72 (m, 2H, 2×Ar—H), 6.92~6.94 (d, 1H, 1×Ar—H), 7.40~7.42 (m, 1H, 1×Ar—H), 8.08 (s, 1H, imidazole-H).

ESI-MS m/z: 358.2[M+1]⁺, calculated: 358.1.

Example 33

Preparation of 4-(3,5-dimethoxyphenyl)-5-(3-hydroxy-4-methoxyphenyl)-imidazole (C118)

The protected 3-hydroxy-4-methoxy-benzaldehyde, anhydrous ethanol, benzyl amine and acetic acid were sequentially added into a three-necked flask, dissolved with stirring, and reacted at reflux. Subsequently, potassium carbonate, isonitrile and tetrahydrofuran were successively added. The mixture was reacted at 50° C. with stirring. After cooling, the ethanol was evaporated under reduced pressure. The residue was purified by silica gel column chromatography to give a solid. Then, the solid was subjected to reduction over palladium on carbon and ammonium formate using methanol as a solvent to afford the desired product, as a white solid, melting point: 181.1~182.4° C.

¹HNMR (CDCl₃) δ (ppm): 3.81-3.84 (m, 6H, 2×OCH₃), 3.96 (s, 3H, 3×OCH₃), 6.39 (m, 2H, 2×Ar—H), 7.06~7.08 (m, 1H, 1×Ar—H), 7.63-7.67 (m, 2H, 2×Ar—H), 7.95 (s, 1H, imidazole-H).

ESI-MS m/z: 327.2 [M+1]⁺, calculated: 327.1.

Example 34

Preparation of 4-(3,5-dimethoxyphenyl)-5-(3-fluoro-4-methoxyphenyl)imidazole (C128)

4-(3,5-Dimethoxyphenyl)-5-(3-fluoro-4-methoxyphenyl)imidazole was prepared according to the method as described in Example 33, as a white solid, melting point: 127.1-128.9° C.

¹HNMR (CDCl₃) δ (ppm): 3.52 (m, 3H, 1×OCH₃), 3.64~3.68 (m, 3H, 1×OCH₃), 3.81~3.84 (s, 3H, OCH₃), 6.33~6.45 (m, 1H, 1×Ar—H), 6.55~6.56 (m, 1H, 1×Ar—H), 6.64 (m, 1H, Ar—H), 6.70~6.85 (m, 1H, 1×Ar—H), 7.10~7.14 (m, 2H, 2×Ar—H), 7.83 (s, 1H, imidazole-H).

ESI-MS m/z: 351.3[M+Na]⁺, calculated: 351.1.

Example 35

Preparation of 4-(3,5-dimethoxyphenyl)-5-(3-amino-4-methoxyphenyl)imidazole (C129)

4-(3,5-Dimethoxyphenyl)-5-(3-amino-4-methoxyphenyl)imidazole was prepared according to the method as described in Example 33, as a white solid, melting point: 135.4~136.9° C.

¹HNMR (CDCl₃) δ (ppm): 3.75~3.77 (m, 6H, 2×OCH₃), 4.01 (s, 3H, 1×OCH₃), 6.44~6.45 (m, 1H, 1×Ar—H), 6.67~6.68 (m, 1H, 1×Ar—H), 7.30~7.32 (m, 2H, 2×Ar—H), 7.59~7.60 (m, 1H, 1×Ar—H), 7.74~7.85 (m, 1H, 1×Ar—H), 8.21 (s, 1H, imidazole-H).

ESI-MS m/z: 326.3[M+1]⁺, calculated: 326.1.

Example 36

Preparation of 4-(3,5-dimethoxyphenyl)-5-(4-dimethylaminophenyl)imidazole (C130)

4-(3,5-Dimethoxyphenyl)-5-(4-dimethylaminophenyl)imidazole was prepared according to the method as described in Example 33, as a white solid, melting point: 79~81.1° C.

¹HNMR (CDCl3) δ (ppm): 2.91 (s, 6H, 2×CH₃), 3.65 (m, 6H, 2×OCH₃), 6.32~6.61 (m, 1H, 1×Ar—H), 6.60~6.74 (m, 4H, 4×Ar—H), 6.28~6.37 (m, 2H, 2×Ar—H), 7.80 (s, 1H, imidazole-H).

ESI-MS m/z: 324.2 [M+1]⁺, calculated: 324.2.

Example 37

Preparation of N-methyl-4-(3,5-dimethoxyphenyl)-5-[(3,4-ethylenedioxyl)thienyl]imidazole (C238)

N-Methyl-4-(3,5-dimethoxyphenyl)-5-[(3,4-ethylenedioxyl)thienyl]imidazole was prepared according to the method as described in Example 30, as a white solid. Melting point: 203~205° C.

¹HNMR (300 MHz, CDCl₃) δ (ppm): 7.67 (s, 1H, imidazole-H), 6.87 (s, 2H, 2×ArH), 6.55 (s, 1H, 1×ArH), 6.34 (s, 1H, 1×ArH), 4.20 (d, 4H, OCH₂CH₂O), 3.736 (s, 6H, 2×OCH₃), 3.60 (s, 3H, 1×N—CH₃).

ESI-MS (m/z): 359.17[M+1]⁺, calculated: 359.20.

Example 38

Preparation of N-methyl-4-(3,5-dimethoxyphenyl)-5-[6-(3-oxobenzomorpholinyl)]imidazole (C252)

N-Methyl-4-(3,5-dimethoxyphenyl)-5-[6-(3-oxobenzomorpholinyl)]imidazole was prepared according to the method as described in Example 30, as a pale yellow solid. Melting point: 218~224° C.

¹HNMR (300 MHz, d-DMSO) δ (ppm): 10.75 (m, 1H, 1×OC—NH—), 7.73 (s, 1H, imidazole-H), 7.08 (m, 1H, 1×Ar—H), 6.95 (m, 1H, 1×Ar—H), 6.84 (m, 1H, 1×Ar—H), 6.59 (m, 2H, 2×Ar—H), 6.26 (s, 1H, Ar—H), 4.64 (s, 2H, 1×O—CH₂—CO), 3.55 (m, 6H, 2×OCH₃), 3.40 (s, 3H, 1×N—CH₃).

ESI-MS (m/z): 366.25[M+1]⁺, calculated 366.14.

Example 39

Preparation of 4-(3,5-dimethoxyphenyl)-5-[6-(3-oxobenzomorpholiny)]oxazole (C253)

4-(3,5-Dimethoxyphenyl)-5-[6-(3-oxobenzomorpholiny)]oxazole was prepared according to the method as described in Example 15, as a pale yellow solid. Melting point: 174~177° C.

¹HNMR (300 MHz, d-DMSO) δ (ppm): 10.84 (s, 1H, 1×OC—NH—), 8.46 (s, 1H, oxazole-H), 7.12 (m, 3H, 1×Ar—H), 6.73 (m, 2H, 2×Ar—H), 6.49 (m, 1H, 1×Ar—H), 4.63 (m, 2H, O—CH₂—CO), 3.70 (m, 6H, 2×OCH₃).

ESI-MS (m/z): 353.26[M+1]⁺, calculated: 353.11.

Example 40

Preparation of N-methyl-4-(3,5-dimethoxyphenyl)-5-(6-benzomorpholinyl)-imidazole (C254)

N-Methyl-4-(3,5-dimethoxyphenyl)-5-(6-benzomorpholinyl)-imidazole was prepared according to the method as described in Example 30, as a pale yellow solid. Melting point: 175~178° C.

¹HNMR (300 MHz, d-DMSO) δ (ppm): 7.67 (s, 1H, imidazole-H), 6.76 (m, 1H, 1×Ar—H), 6.66 (s, 2H, 2×Ar—H), 6.50 (s, 1H, 1×Ar—H), 6.45 (m, 1H, 1×Ar—H), 6.22 (s, 1H, 1×Ar—H), 5.89 (s, 1H, —NH—), 4.15 (m, 2H, 1×O—CH$_2$—), 3.58 (s, 6H, 2×OCH$_3$), 3.39 (s, 3H, 1×-NCH$_3$), 3.29 (m, 2H, 1×-CH$_2$—N—).

ESI-MS (m/z): 352.25[M+1]$^+$, Calculated: 352.16.

Example 41

Preparation of 4-(3,5-dimethoxyphenyl)-5-(6-benzomorpholinyl)oxazole (C255)

4-(3,5-Dimethoxyphenyl)-5-(6-benzomorpholinyl)oxazole was prepared according to the method as described in Example 30, as white crystals. Melting point: 175-178° C.

$^1$HNMR (300 MHz, d-DMSO) δ (ppm): 8.46 (s, 1H, oxazole-H), 7.12 (m, 3H, Ar—H), 6.73 (s, 2H, 2×Ar—H), 6.49 (s, 1H, 1×Ar—H), 5.89 (s, 1H, —NH—), 4.15 (m, 2H, O—CH$_2$—), 3.70 (s, 6H, 2×OCH$_3$), 3.29 (m, 2H, —CH$_2$—N).

ESI-MS (m/z): 339.36[M+1]$^+$, calculated: 339.13.

Example 42

Preparation of N-hydroxyethyl-4-(3,5-dimethoxyphenyl)-5-(3-fluoro-4-methoxyphenyl)imidazole (C256)

3-Fluoro-4-methylbenzaldehyde (1.0 g, 6.49 mmol) and 30 mL anhydrous dichloromethane were added into a 100 mL three-necked flask and dissolved with stirring Anhydrous calcium chloride (6.0 g) and ethanolamine (1.7 g) were added, and the reaction lasted for 3-4 days at room temperature. The solid was filtered off, and the filtrate was concentrated under reduced pressure to obtain a light yellow solid residue. The residue was dissolved by adding 50 mL anhydrous ethanol. Then, 1-p-toluenesulfonyl-1-(3,5-dimethoxyphenyl) methyl isonitrile 2.6 g (8 mmol) and anhydrous THF (40 mL), tert-butylamine (2.4 mL) were added in succession, and the reaction lasted at 25-35° C. for 40 hours with stirring. The mixture was concentrated under reduced pressure, and the residue was washed by addition of 40 mL ethyl acetate, filtered and dried by suction to give a pale yellow solid, which was further purified by silica gel column chromatography (ethyl acetate:methanol=25:1) to afford the desired compound, as a white solid. Melting point: 202~204° C.

$^1$HNMR (300 MHz, d-DMSO) δ (ppm): 7.76 (s, 1H, imidazole-H), 7.29 (m, 2H, 2×Ar—H), 7.14 (m, 1H, 1×Ar—H), 6.52 (s, 2H, 2×Ar—H), 6.25 (s, 1H, Ar—H), 3.89 (s, 3H, 1×OCH$_3$), 3.79 (m, 2H, 1×-NCH$_2$—), 3.57 (s, 6H, 2×OCH$_3$), 3.45 (m, 2H, 1×-CH$_2$—OH).

ESI-MS (m/z): 373.25[M+1]$^+$, calculated: 373.39.

Example 43

Preparation of N-hydroxyethyl-4-(3,5-dimethoxyphenyl)-5-[(3,4-ethylenedioxyl)thienyl]imidazole (C257)

N-Hydroxyethyl-4-(3,5-dimethoxyphenyl)-5-[(3,4-ethylenedioxyl)thienyl]imidazole was prepared according to the method as described in Example 42, as a yellow solid. Melting point: 183~185° C.

$^1$HNMR (300 MHz, CDCl$_3$) δ (ppm): 7.70 (s, 1H, imidazole-H), 6.78 (s, 2H, 2×ArH), 6.49 (s, 1H, 1×ArH), 6.33 (s, 1H, 1×ArH), 4.13-4.05 (d, 4H, OCH$_2$CH$_2$O), 3.90 (t, 2H, 1×-CH$_2$—OH), 3.73 (t, 2H, 1×-NCH$_2$—), 3.70 (s, 6H, 2×OCH$_3$).

ESI-MS (m/z): 389.08[M+1]$^+$, calculated: 389.11.

Example 44

Preparation of N-benzyl-4-(3,5-dimethoxyphenyl)-5-[(3,4-ethylenedioxyl)thienyl]imidazole (C258)

3,4-Ethylenedioxyl thiophene aldehyde (0.60 g, 3.5 mmol), benzylamine (0.5 mL, 4.6 mmol), 2.5 g anhydrous calcium chloride and 30 mL anhydrous dichloromethane were added into a 100 mL three-necked flask, and the reaction lasted at room temperature for 8 hours. Calcium chloride was filtered off, and dichloromethane was evaporated under reduced pressure to give the corresponding imine compound. 1-p-Toluenesulfonyl-1-(3,5-dimethoxyphenyl)methyl isonitrile (0.8 g, 2.4 mmol), 50 mL anhydrous ethanol, 15 mL anhydrous THF, 0.8 g (3.2 mmol) imine, and 1.0 mL tert-butylamine were added into a 100 mL round-bottomed flask. The mixture was stirred at room temperature for 12 hours, while the reaction was monitored by TLC. After concentration, the residue was purified by silica gel column chromatography (ethyl acetate:methanol=100:1) to give a pale yellow solid. Melting point: 149~152° C.

$^1$HNMR (300 MHz, CDCl$_3$) δ (ppm): 7.67 (s, 1H, imidazole-H), 7.27~7.30 (m, 3H, 3×ArH), 7.05 (m, 2H, 2×ArH), 6.89 (s, 2H, 2×ArH), 6.48 (s, 1H, 1×ArH), 6.33 (s, 1H, 1×ArH), 5.03 (s, 2H, 1×Ar CH$_2$N), 4.08-3.92 (d, 4H, OCH$_2$CH$_2$O), 3.72 (s, 6H, 2×OCH$_3$).

ESI-MS (m/z): 435.17[M+1]$^+$, calculated: 435.13.

Example 45

Preparation of N-methyl-4-(3,5-dimethoxyphenyl)-5-(3,4,5-trifluorophenyl)imidazole (C262)

N-Methyl-4-(3,5-dimethoxyphenyl)-5-(3,4,5-trifluorophenyl)imidazole was prepared according to the method as described in Example 30, as a white solid. Melting point: 159~160° C.

$^1$HNMR (300 MHz, CDCl$_3$) δ: 3.51 (s, 3H, 1×N—CH$_3$), 3.71 (s, 6H, 2×O—CH$_3$), 6.32 (m, 1H, 1×Ar—H), 6.62 (m, 2H, 2×Ar—H), 7.00 (m, 2H, 2×Ar—H), 7.58 (s, 1H, imidazole-H).

ESI-MS (m/z): 349.17[M+1]$^+$, calculated: 349.11.

Example 46

Preparation of N-methyl-4-(3,5-dimethoxyphenyl)-5-(3,5-difluoro-4-methylaminophenyl)imidazole (C263)

C263 was separated simultaneously during the preparation of C262. Melting point: 155~157° C.

$^1$HNMR (300 MHz, CDCl$_3$) δ: 3.12 (s, 3H, 1×NH—CH$_3$), 3.49 (s, 3H, 1×N—CH$_3$), 3.71 (s, 6H, 2×O—CH$_3$), 6.32 (s, 1H 1×Ar—H), 6.72 (m, 2H, 2×Ar—H), 6.82 (m, 2H, 2×Ar—H), 7.60 (s, 1H, imidazole-H).

ESI-MS (m/z): 360.25[M+1]$^+$, calculated: 360.15.

Example 47

Preparation of 4-(3,5-dimethoxyphenyl)-5-(3-fluoro-4-methylaminophenyl)oxazole (C264)

4-(3,5-Dimethoxyphenyl)-5-(3-fluoro-4-methylaminophenyl)oxazole was prepared according to the method as described in Example 15, as a white solid. Melting point: 140~142° C.

¹HNMR (300 MHz, CDCl₃) δ: 3.48 (s, 3H, 1×N—CH₃), 3.68 (s, 6H, 2×O—CH₃), 6.31 (m, 1H 1×Ar—H), 6.61 (m, 2H, 2×Ar—H), 7.10~7.18 (m, 2H, 2×Ar—H), 7.28 (m, 1H, 1×Ar—H), 7.59 (s, 1H, imidazole-H).

ESI-MS (m/z): 329.5[M+1]⁺, calculated: 329.1.

Example 48

Preparation of N-methyl-4-(3,5-dimethoxyphenyl)-5-[6-benzo(N-methylmorpholine)]imidazole (C265)

N-Methyl-4-(3,5-dimethoxyphenyl)-5-[6-benzo(N-methylmorpholine)]imidazole was prepared according to the method as described in Example 30, as a white solid. Melting point: 125~127° C.

¹HNMR (300 MHz, CDCl₃) δ (ppm): 7.60 (s, 1H, imidazole-H), 6.84 (d, 1H, 1×Ar—H), 6.80 (s, 2H, 2×Ar—H), 6.39 (d, 1H, 1×Ar—H), 6.58 (s, 1H, 1×Ar—H), 6.28 (s, 1H, 1×Ar—H), 4.34 (t, 2H, —O—CH₂), 3.66 (s, 6H, 2×OCH₃) 3.49 (s, 3H, 1×CH₃), 3.29 (t, 2H, —N—CH₂), 2.80 (s, 3H, 1×CH₃).

ESI-MS (m/z): 366.3[M+1]⁺, calculated: 366.2.

Example 49

Preparation of 4-(3,5-dimethoxyphenyl)-5-[6-benzo(N-methylmorpholine)]oxazole (C266)

4-(3,5-Dimethoxyphenyl)-5-[6-benzo(N-methylmorpholine)]oxazole was prepared according to the method as described in Example 15, as a reddish brown oil.

¹HNMR (300 MHz, CDCl₃) δ (ppm): 7.90 (s, 1H, oxazole-H), 6.96-6.99 (m, 2H, 2×ArH), 6.89 (s, 1H, 1×Ar—H), 6.88 (s, 1H, 1×Ar—H), 6.77 (d, 1H, 1×Ar—H), 6.44 (s, 1H, 1×Ar—H), 4.34 (t, 2H, —O—CH₂), 3.77 (s, 6H, OCH₃), 3.29 (t, 2H, —N—CH₂), 2.83 (s, 3H, 1×N—CH₃).

ESI-MS (m/z):353.3[M+1]⁺, calculated: 353.2.

Example 50

Preparation of 4-(3,5-dimethoxyphenyl)-5-(3-fluoro-4-methylaminophenyl)imidazole (C267)

4-(3,5-Dimethoxyphenyl)-5-(3-fluoro-4-methylaminophenyl)imidazole was prepared according to the method as described in Example 33, as a light yellow solid. Melting point: 182~184° C.

¹HNMR (300 MHz, CDCl₃) δ: 2.88 (s, 3H, 1×N—CH₃), 3.69 (s, 6H, 2×O—CH₃), 6.39 (m, 1H, 1×Ar—H), 6.59 (m, 1H, 1×Ar—H), 6.70 (m, 2H, 2×Ar—H), 7.15 (m, 2H, 2×Ar—H) 7.59 (s, 1H, imidazole-H).

ESI-MS (m/z): 328.3[M+1]⁺, calculated: 328.1.

Example 51

Preparation of N-methyl-4-(3,4,5-trimethoxyphenyl)-5-[(3,4-dimethoxy)thienyl]imidazole (C259)

N-Methyl-4-(3,4,5-trimethoxyphenyl)-5-[(3,4-dimethoxy)thienyl]imidazole was prepared according to the method as described in Example 30, as a white solid. Melting point: 142~143° C.

¹HNMR (300 MHz, CDCl₃) δ (ppm): 3.55 (s, 3H, 1×N—CH₃), 3.60 (s, 3H, 1×O—CH₃), 3.76 (s, 6H, 2×O—CH₃), 3.83 (s, 3H, 1×O—CH₃), 3.89 (s, 3H O—CH₃), 6.39 (s, 1H, Thiophene), 6.98 (s, 2H, 2×Ar—H), 7.64 (s, 1H, imidazole-H).

ESI-MS (m/z): 391.25[M+1]⁺, calculated: 391.13.

Example 52

Preparation of N-hydroxyethyl-4-(3,4,5-trimethoxyphenyl)-5-[(3,4-dimethoxy)thienyl]imidazole (C260)

N-Hydroxyethyl-4-(3,4,5-trimethoxyphenyl)-5-[(3,4-dimethoxy)thienyl]imidazole was prepared according to the method as described in Example 42, as a white solid. Melting point: 145~146° C.

¹HNMR (300 MHz, CDCl₃) δ (ppm): 3.53 (s, 3H, 1×O—CH₃), 3.74 (s, 6H, 2×O—CH₃), 3.84 (t, 2H, N—CH₂), 3.86 (s, 6H, 2×O—CH₃), 3.99 (t, 2H, O—CH₂), 6.36 (s, 1H, Thiophene), 6.92 (m, 2H, 2×Ar—H), 7.97 (s, 1H, imidazole-H).

ESI-MS (m/z): 421.25[M+1]⁺, calculated: 421.14.

Example 53

Preparation of N-benzyl-4-(3,4,5-trimethoxyphenyl)-5-[(3,4-dimethoxy)thienyl]imidazole (C261)

N-Benzyl-4-(3,4,5-trimethoxyphenyl)-5-[(3,4-dimethoxy)thienyl]imidazole was prepared according to the method as described in Example 44, as a white solid. Melting point: 114~115° C.

¹HNMR (300 MHz, CDCl₃) δ: 3.45 (s, 3H, 1×O—CH₃), 3.78 (s, 6H, 2×O—CH₃), 3.83 (s, 3H, 1×O—CH₃), 3.87 (s, 3H, 1×O—CH₃), 5.03 (s, 2H, NCH₂Ph), 6.36 (s, 1H, Thiophene), 6.98 (m, 2H, 1×Ar—H), 7.10 (m, 2H, 2×Ar—H) 7.30 (m, 3H, 3×Ar—H), 7.67 (s, 1H, imidazole-H).

ESI-MS (m/z): 467.33[M+1]⁺, calculated: 467.16.

Example 54

Preparation of N-hydroxyethyl-4-(3,4,5-trimethoxyphenyl)-5-(4-trifluoromethylphenyl)imidazole (C239)

N-Hydroxyethyl-4-(3,4,5-trimethoxyphenyl)-5-(4-trifluoromethylphenyl)imidazole was prepared according to the method as described in Example 42, as a pale yellow solid. Melting point: 208~210° C.

¹HNMR (300 MHz, CDCl₃) δ: 3.55 (s, 6H, 2×OCH₃), 3.73 (m, 2H, N—CH₂—), 3.82 (m, 2H, O—CH₂—), 3.84 (s, 3H, 1×OCH₃), 6.52 (s, 2H, 2×Ar—H), 7.12 (d, 2H, 2×Ar—H), 7.59 (d, 2H, 2×Ar—H), 7.77 (s, 1H, imidazole-H).

ESI-MS (m/z): 423.17[M+1]⁺, calculated: 423.15.

Example 55

Preparation of N-methyl-4-(3,4,5-trimethoxyphenyl)-5-(4-trifluoromethylphenyl)imidazole (C240)

N-Methyl-4-(3,4,5-trimethoxyphenyl)-5-(4-trifluoromethylphenyl)imidazole was prepared according to the method as described in Example 30, as a white solid. Melting point: 168~171° C. ¹HNMR (300 MHz, CDCl₃) δ: 3.55 (s, 3H, 1×N—CH₃), 3.62 (s, 6H, 2×OCH₃), 3.81 (s, 3H, 1×OCH₃), 6.65 (s, 2H, 2×Ar—H), 7.53 (d, 2H, 2×Ar—H), 7.68 (s, 1H, imidazole-H), 7.76 (d, 2H, 2×Ar—H).

ESI-MS (m/z): 393.17[M+1]$^+$, calculated: 393.14.

Example 56

Preparation of N-cyclopropyl-4-(3,4,5-trimethoxyphenyl)-5-(4-trifluoromethylphenyl)imidazole (C243)

To a 100 mL dry three-necked flask equipped with a mechanical stirrer, a condenser and a calcium chloride drying tube were passed nitrogen gas and added 20 mL freshly dried anhydrous ethanol and 3.00 g (52.8 mmol) cyclopropylamine while stirring, followed by Addition of 3.5 g (58 mmol) glacial acetic acid dropwise under ice-water cooling. After the completion, the solution was warmed to room temperature and stirred for 15 minutes, and 0.7 g (1.76 mmol) N-[(1-(3,4,5-trimethoxyphenyl)-2-(4-trifluoromethylphenyl)formyl)]formamide was added, and while stirring to dissolve, the solution was heated at reflux for about 4 hours. After the reaction was completed, most of the ethanol was distilled off under reduced pressure, about 100 ml cold water was added, and a small amount of aqueous ammonia was added dropwise till the solution had a pH of about 7-8, and a yellow viscous matter was precipitated. The resultant mixture was extracted with dichloromethane, dried over anhydrous sodium sulfate, filtered, and concentrated to give the crude product, which was further purified by silica gel column chromatography (ethyl acetate:petroleum ether=1:1) to afford a yellow solid. Melting point: 125~130° C.

$^1$HNMR (300 MHz, CDCl$_3$) δ: 0.87 (m, 4H, 1×-CH$_2$CH$_2$—), 3.18 (m, 1H, 1×N—CH), 3.61 (s, 6H, 2×OCH$_3$), 3.80 (s, 3H, 1×OCH$_3$), 6.63 (s, 2H, 2×ArH), 7.57 (d, J=8.1 Hz, 2H, 2×ArH), 7.63 (s, 1H, imidazole-H), 7.73 (d, J=8.1 Hz, 2H, 2×ArH).

ESI-MS (m/z): 419.17[M+1]$^+$, calculated: 418.15.

Example 57

Preparation of 4-(3,4,5-trimethoxyphenyl)-5-(4-trifluoromethylphenyl)thiazole (C244)

To a 100 mL dry three-necked flask equipped with a mechanical stirrer, a condenser and a calcium chloride drying tube were passed nitrogen gas and added 0.7 g (1.76 mmol) N-[(1-(3,4,5-trimethoxyphenyl)-2-(4-trifluoromethylphenyl)formyl)]carboxamide, 1.1 g (2.64 mmol) Lawesson's reagent (LR) and 40 mL dry toluene while stirring. The solution was heated at reflux for 7 hours. After the reaction was completed, the solution was cooled to room temperature, and the white insolubles were removed by filtration. The filtrate was mixed with 40 mL sodium hydroxide solution (25%) for 30 minutes with stirring. The organic layer was separated, washed three times with brine (40 mL×3), dried over anhydrous sodium sulfate, and the solvent was evaporated under reduced pressure to give a yellow residue, which was further purified by silica gel column chromatography (ethyl acetate: petroleum ether:triethylamine=100:150:3) to afford a pale yellow powder. Melting point: 110~113° C.

$^1$HNMR (300 MHz, CDCl$_3$) δ: 3.67 (s, 6H, 2×OCH$_3$), 3.86 (s, 3H, 1×OCH$_3$), 6.71 (s, 2H, 2×Ar—H), 7.53 (d, J=8.1 Hz, 2H, 2×Ar—H), 7.63 (d, J=8.1 Hz, 2H, 2×Ar—H), 8.87 (s, 1H, Thiazole-H).

ESI-MS (m/z): 396.08[M+1]$^+$, calculated: 396.08.

Example 58

Preparation of N-ethoxycarbonylmethyl-4-(3,4,5-trimethoxyphenyl)-5-(4-trifluoromethylphenyl)imidazole (C245)

To a three-necked flask protected with nitrogen gas was added 9.416 g (75 mmol) glycine methyl ester hydrochloride, which was suspended in 50 mL anhydrous methanol. Triethylamine (7.6 g) was added dropwise to neutralize hydrogen chloride, and the mixture was stirred for 20 minutes and filtered to remove insolubles. The filtrate was added to a 100 ml three-necked flask equipped with a mechanical stirrer, a condenser and a calcium chloride drying tube, purged with nitrogen gas, and while stirring, 4.5 g (75 mmol) glacial acetic acid was added dropwise under ice-water cooling. After completion of the addition, the solution was warmed to room temperature and stirred for 15 minutes. Subsequently, 1.0 g (2.5 mmol) N-[(1-(3,4,5-trimethoxyphenyl)-2-(4-trifluoromethylphenyl)formyl)]formamide was added, and the mixture was heated at reflux for about 7 hours. After the reaction was completed, the insolubles were filtered off, and most of the solvent was distilled off under reduced pressure to give a yellow viscous material, which was dissolved in 50 mL ethyl acetate, washed with water, and dried over anhydrous sodium sulfate. The solvent was evaporated, and the residue was purified by silica gel column chromatography (ethyl acetate) to give a pale yellow solid. Melting point: 129~134° C.

$^1$HNMR (300 MHz, CDCl$_3$) δ: 3.60 (s, 6H, 2×OCH$_3$), 3.72 (s, 3H, 1×OCH$_3$), 3.80 (s, 3H, 1×-OCH$_3$), 4.56 (s, 2H, 1×N—CH$_2$), 6.63 (s, 2H, 2×Ar—H), 7.50 (d, J=8.1 Hz, 2H, 2×Ar—H), 7.66 (s, 1H, imidazole-H), 7.74 (d, J=8.1 Hz, 2H, 2×Ar—H).

ESI-MS (m/z): 451.17[M+1]$^+$, calculated: 451.14.

Example 59

Preparation of N-hydroxyethyl-4-(3,4,5-trimethoxyphenyl)-5-[(3,4-ethylenedioxyl)thienyl]imidazole (C246)

N-Hydroxyethyl-4-(3,4,5-trimethoxyphenyl)-5-[(3,4-ethylenedioxyl)thienyl]imidazole was prepared according to the method as described in Example 42, as a pale yellow solid. Melting point: 166~168° C.

$^1$HNMR (300 MHz, CDCl$_3$) δ (ppm): 7.70 (s, 1H, imidazole-H), 6.83 (s, 2H, 2×Ar—H), 6.46 (s, 1H, Ar—H), 4.12~4.02 (d, 4H, 1×OCH$_2$CH$_2$O), 3.89 (t, 2H, 1×O—CH$_2$), 3.83 (s, 3H, 1×OCH$_3$), 3.76~3.72 (m, 8H, 1×N—CH$_2$, 2×OCH$_3$).

ESI-MS (m/z): 419.2[M+1]$^+$, calculated: 419.12.

Example 60

Preparation of N-benzyl-4-(3,4,5-trimethoxyphenyl)-5-[(3,4-ethylenedioxyl)thienyl]imidazole (C247)

N-Benzyl-4-(3,4,5-trimethoxyphenyl)-5-[(3,4-ethylenedioxyl)thienyl]imidazole was prepared according to the method as described in Example 44, as a yellow solid. Melting point: 153~156° C.

$^1$HNMR (300 MHz, CDCl$_3$) δ (ppm): 7.69 (s, 1H, imidazole-H), 7.27 (m, 2H, 2×Ar—H), 7.05 (m, 2H, 2×Ar—H), 6.95 (m, 2H, 2×Ar—H), 6.49 (s, 1H, Ar—H), 5.03 (s, 2H, N—CH$_2$), 4.09~3.92 (d, 4H, OCH$_2$CH$_2$O), 3.82 (s, 3H, 1×OCH$_3$), 3.75 (s, 6H, 2×OCH$_3$).

ESI-MS (m/z): 465.17[M+1]$^+$, calculated: 465.14.

Example 61

Preparation of N-hydroxyethyl-4-(3,4,5-trimethoxyphenyl)-5-[4-(2,2'-dichlorodiethylamine)phenylimidazole (C248)

N-Hydroxyethyl-4-(3,4,5-trimethoxyphenyl)-5-[4-(2,2'-dichlorodiethylamine)phenylimidazole was prepared according to the method as described in Example 42, as a white solid. Melting point: 170~171° C.

$^1$HNMR (300 MHz, CDCl$_3$) δ (ppm): 7.72 (s, 1H, imidazole-H), 7.73~6.55 (m, 4H, 4×ArH), 6.63 (s, 2H, 2×ArH), 3.85~3.59 (m, 21H, 3×OCH$_3$, 3×NCH$_2$, 2×ClCH$_2$, OCH$_2$).

ESI-MS (m/z): 494.17[M+1]$^+$, 494.15.

Example 62

Preparation of N-methyl-4-(3,4,5-trimethoxyphenyl)-5-[6-(3-oxobenzomorpholine)]imidazole (C249)

N-Methyl-4-(3,4,5-trimethoxyphenyl)-5-[6-(3-oxobenzomorpholine)]imidazole was prepared according to the method as described in Example 30, as a pale yellow solid. Melting point: 233~235° C.

$^1$HNMR (300 MHz, d-DMSO) δ (ppm): 10.76 (s, 1H, OC—NH—), 7.73 (s, 1H, imidazole), 7.11 (s, 1H, Ar—H), 7.00 (m, 1H, Ar—H), 6.85 (m, 1H, Ar—H), 6.71 (s, 2H, 2×Ar—H), 4.63 (s, 2H, O—CH$_2$—CO), 3.6 (s, 3H, OCH$_3$), 3.55 (s, 6H, 2×OCH$_3$), 3.42 (s, 3H, —NCH$_3$).

ESI-MS (m/z): 396.25[M+1]$^+$, calculated 396.15.

Example 63

Preparation of N-hydroxyethyl-4-(3,4,5-trimethoxyphenyl)-5-[6-(3-oxobenzomorpholinyl)]imidazole (C250)

N-Hydroxyethyl-4-(3,4,5-trimethoxyphenyl)-5-[6-(3-oxobenzomorpholinyl)]imidazole was prepared according to the method as described in Example 42, as a white solid. Melting point: 189~191° C.

$^1$HNMR (300 MHz, d-DMSO) δ (ppm): 10.78 (s, 1H, 1×OC—NH—), 7.75 (s, 1H, imidazole), 7.11 (s, 1H, 1×Ar—H), 6.99 (m, 1H, 1×Ar—H), 6.85 (m, 1H, 1×Ar—H), 6.68 (s, 2H, 2×Ar—H), 4.96 (1H, —OH), 4.63 (s, 2H, O—CH$_2$—CO), 3.80 (m, 2H, —NCH$_2$—), 3.59 (s, 3H, OCH$_3$), 3.54 (s, 6H, 2×OCH$_3$), 3.48 (m, 2H, —CH$_2$—OH).

ESI-MS (m/z): 426.17[M+1]$^+$, calculated 426.16.

Example 64

Preparation of N-methyl-4-(3,4,5-trimethoxyphenyl)-5-(6-benzomorpholinyl)imidazole (C251)

N-Methyl-4-(3,4,5-trimethoxyphenyl)-5-(6-benzomorpholinyl)imidazole was prepared according to the method as described in Example 30, as white crystals. Melting point: 160~162° C.

$^1$HNMR (300 MHz, d-DMSO) δ (ppm): 8.40 (s, 1H, imidazole), 6.75 (s, 2H, 2×Ar—H), 6.71 (m, 1H, 1×Ar—H), 6.48 (m, 2H, 2×Ar—H), 5.91 (m, 1H, 1×-NH—), 4.11 (m, 2H, 1×O—CH$_2$—), 3.64 (s, 3H, 1×OCH$_3$), 3.58 (s, 6H, 2×OCH$_3$), 3.50 (s, 3H, 1×N—CH$_3$), 3.24 (m, 2H, 1×-CH$_2$—N).

ESI-MS (m/z): 382.25[M+1]$^+$, calculated 382.17.

Example 65

Preparation of 4-(3,5-dimethoxyphenyl)-5-(2-hydroxy-3-amino-4-methoxyphenyl)oxazole (C141)

4-(3,5-Dimethoxyphenyl)-5-(2-hydroxy-3-amino-4-methoxyphenyl)oxazole was prepared according to the method as described in Example 15, as a yellow solid, melting point: 152.1~154.0° C.

$^1$HNMR (CDCl3) δ (ppm): 3.69 (s, 6H, 2×OCH$_3$), 3.90 (s, 3H, 1×OCH$_3$), 5.65 (s, 1H, 1×O—H), 6.31~6.32 (t, 1H, 1×Ar—H), 6.52~6.54 (d, 1H, 1×Ar—H), 6.82~6.83 (d, 2H, 2×Ar—H), 6.92~6.94 (d, 1H, 1×Ar—H), 7.91 (s, 1H, oxazole-H).

ESI-MS m/z: 343.3[M+1]$^+$, calculated: 343.1.

Example 66

Preparation of 4-(3,5-dimethoxyphenyl)-5-(3-hydroxy-4-trifluoromethoxyphenyl)oxazole (C142)

4-(3,5-Dimethoxyphenyl)-5-(3-hydroxy-4-trifluoromethoxyphenyl)oxazole was prepared according to the method as described in Example 15, as a yellow solid, melting point: 192.2~194.3° C.

$^1$HNMR (CDCl$_3$) δ (ppm): 3.96 (s, 6H, 2×OCH$_3$), 6.92~6.99 (d, 1H, 1×Ar—H), 7.45 (d, 1H, 1×Ar—H), 7.77 (d, 2H, 2×Ar—H), 7.82~7.91 (d, 2H, 2×Ar—H), 8.02 (s, 1H, oxazole-H).

ESI-MS m/z: 382.1[M+1]$^+$, calculated: 382.1.

Example 67

Preparation of 4-(3,5-dimethoxyphenyl)-5-(3-hydroxy-4-difluoromethoxyphenyl)oxazole (C143)

4-(3,5-Dimethoxyphenyl)-5-(3-hydroxy-4-difluoromethoxyphenyl)oxazole was prepared according to the method as described in Example 15, as a yellow oil.

$^1$HNMR (CDCl$_3$) δ (ppm): 3.67 (s, 6H, 2×OCH$_3$), 3.86 (s, 1H, OCF$_2$H), 5.61 (s, 1H, 1×O—H), 6.35~6.36 (t, 1H, 1×Ar—H), 6.57~6.59 (d, 2H, 2×Ar—H), 6.82~6.83 (d, 2H, 2×Ar—H), 6.92~6.94 (d, 1H, Ar—H), 7.91 (s, 1H, oxazole-H).

ESI-MS m/z: 364.1[M+1]$^+$, calculated: 364.1.

Example 68

Preparation of 4-(3,5-dimethoxyphenyl)-5-(2-hydroxy-3-hydroxy-4-methoxyphenyl)imidazole (C144)

4-(3,5-Dimethoxyphenyl)-5-(2-hydroxy-3-hydroxy-4-methoxyphenyl)imidazole was prepared according to the method as described in Example 33, as a yellow solid, melting point: 132.1~134.0° C.

$^1$HNMR (CDCl$_3$) δ (ppm): 3.69 (s, 6H, 2×OCH$_3$), 3.90 (s, 3H, 1×OCH$_3$), 5.65 (s, 1H, 1×O—H), 5.75 (s, 1H, 1×O—H), 6.31~6.32 (t, 1H, 1×Ar—H), 6.52~6.54 (d, 1H, 1×Ar—H), 6.82~6.83 (d, 2H, 2×Ar—H), 6.92~6.94 (d, 1H, 1×Ar—H), 7.91 (s, 1H, imidazole-H).

ESI-MS m/z: 343.2[M+1]⁺, calculated: 343.1.

Example 69

Preparation of 4-(3,5-dimethoxyphenyl)-5-(2-amino-3-amino-4-methoxyphenyl)imidazole (C145)

4-(3,5-Dimethoxyphenyl)-5-(2-amino-3-amino-4-methoxyphenyl)imidazole was prepared according to the method as described in Example 33, as a yellow solid, melting point: 112.1~114.2° C.

$^1$HNMR (CDCl$_3$) δ (ppm): 3.54 (s, 6H, 2×OCH$_3$), 3.85 (s, 3H, 1×OCH$_3$), 6.27~6.29 (t, 1H, 1×Ar—H), 6.44~6.47 (d, 1H, 1×Ar—H), 6.74~6.76 (d, 2H, 2×Ar—H), 6.88~6.90 (d, 1H, 1×Ar—H), 7.82 (s, 1H, imidazole-H).

ESI-MS m/z: 341.2[M+1]⁺, calculated: 341.2.

Example 70

Preparation of 4-(3,5-dimethoxyphenyl)-5-(2-hydroxy-3-amino-4-methoxyphenyl)imidazole (C146)

4-(3,5-Dimethoxyphenyl)-5-(2-hydroxy-3-amino-4-methoxyphenyl)imidazole was prepared according to the method as described in Example 33, as a yellow solid, melting point: 132.1~133.9° C.

$^1$HNMR (CDCl$_3$) δ (ppm): 3.84 (s, 6H, 2×OCH$_3$), 3.96 (s, 3H, 1×OCH$_3$), 5.44 (s, 1H, 1×O—H), 6.46~6.48 (t, 1H, 1×Ar—H), 6.59~6.61 (d, 1H, 1×Ar—H), 6.79~6.81 (d, 2H, 2×Ar—H), 6.95~6.97 (d, 1H, 1×Ar—H), 7.75 (s, 1H, imidazole-H).

ESI-MS m/z: 342.2[M+1]⁺, calculated: 342.1.

Example 71

Preparation of 4-(3,5-dimethoxyphenyl)-5-(2-amino-3-hydroxy-4-methoxyphenyl)imidazole (C147)

4-(3,5-Dimethoxyphenyl)-5-(2-amino-3-hydroxy-4-methoxyphenyl)imidazole was prepared according to the method as described in Example 33, as a yellow solid, melting point: 147.6~148.2° C.

$^1$HNMR (CDCl$_3$) δ (ppm): 3.76 (s, 6H, 2×OCH$_3$), 3.89 (s, 3H, 1×OCH$_3$), 5.59 (s, 1H, 1×O—H), 6.47~6.50 (t, 1H, 1×Ar—H), 6.59~6.62 (d, 1H, 1×Ar—H), 6.88~6.90 (d, 2H, 2×Ar—H), 6.96~6.98 (d, 1H, 1×Ar—H), 7.58 (s, 1H, imidazole-H).

ESI-MS m/z: 342.2[M+1]⁺, calculated: 342.2.

Example 72

Preparation of 4-(3,5-dimethoxyphenyl)-5-(2-fluoro-3-hydroxy-4-methoxyphenyl)imidazole (C148)

4-(3,5-Dimethoxyphenyl)-5-(2-fluoro-3-hydroxy-4-methoxyphenyl)imidazole was prepared according to the method as described in Example 33, as a white solid, melting point: 126.5~128.2° C.

$^1$HNMR (CDCl$_3$) δ (ppm): 3.58 (s, 6H, 2×OCH$_3$), 3.79 (s, 3H, 1×OCH$_3$), 5.48 (s, 1H, 1×O—H), 6.39~6.42 (t, 1H, 1×Ar—H), 6.48~6.49 (d, 1H, 1×Ar—H), 6.78~6.79 (d, 2H, 2×Ar—H), 6.82~6.84 (d, 1H, 1×Ar—H), 7.86 (s, 1H, imidazole-H).

ESI-MS m/z: 345.3[M+1]⁺, calculated: 345.1.

Example 73

Preparation of 4-(3,5-dimethoxyphenyl)-5-(2-fluoro-3-amino-4-methoxyphenyl)imidazole (C149)

4-(3,5-Dimethoxyphenyl)-5-(2-fluoro-3-amino-4-methoxyphenyl)imidazole was prepared according to the method as described in Example 33, as a yellow solid, melting point: 118.2~119.7° C.

$^1$HNMR (CDCl$_3$) δ (ppm): 3.75 (s, 6H, 2×OCH$_3$), 3.89 (s, 3H, 1×OCH$_3$), 6.44~6.45 (t, 1H, 1×Ar—H), 6.59~6.62 (d, 1H, 1×Ar—H), 6.78~6.80 (d, 2H, 2×Ar—H), 6.89~6.91 (d, 1H, 1×Ar—H), 7.88 (s, 1H, imidazole-H).

ESI-MS m/z: 344.2[M+1]⁺, calculated: 344.1.

Example 74

Preparation of 4-(3,5-dimethoxyphenyl)-5-(3-hydroxy-4-trifluoromethoxyphenyl)imidazole (C150)

4-(3,5-Dimethoxyphenyl)-5-(3-hydroxy-4-trifluoromethoxyphenyl) imidazole was prepared according to the method as described in Example 33, as a yellow oil.

$^1$HNMR (CDCl$_3$) δ (ppm): 3.89 (s, 6H, 2×OCH$_3$), 6.58~6.61 (d, 1H, 1×Ar—H), 7.45 (d, 1H, 1×Ar—H), 7.77 (d, 2H, 2×Ar—H), 7.82~7.91 (d, 2H, 2×Ar—H), 7.98 (s, 1H, imidazole-H).

ESI-MS m/z: 381.1[M+1]⁺, calculated: 381.1.

Example 75

Preparation of 4-(3,5-dimethoxyphenyl)-5-(3-hydroxy-4-difluoromethoxyphenyl) imidazole (C151)

4-(3,5-Dimethoxyphenyl)-5-(3-hydroxy-4-difluoromethoxyphenyl) imidazole was prepared according to the method as described in Example 33, as a white solid, melting point: 159.2~161.3° C.

$^1$HNMR (CDCl$_3$) δ (ppm): 3.67 (s, 6H, 2×OCH$_3$), 4.26 (s, 1H, OCF$_2$H), 5.61 (s, 1H, 1×O—H), 6.35~6.36 (t, 1H, 1×Ar—H), 6.57~6.59 (d, 2H, 2×Ar—H), 6.82~6.83 (d, 2H, 2×Ar—H), 6.92~6.94 (d, 1H, 1×Ar—H), 7.91 (s, 1H, imidazole-H).

ESI-MS m/z: 363.1[M+1]⁺, calculated: 363.1.

Example 76

Preparation of 4-(3,5-dimethoxyphenyl)-5-(3-amino-4-trifluoromethoxyphenyl)imidazole (C152)

4-(3,5-Dimethoxyphenyl)-5-(3-amino-4-trifluoromethoxyphenyl)imidazole was prepared according to the method as described in Example 33, as a yellow solid, melting point: 182.0~183.8° C.

$^1$HNMR (CDCl$_3$) δ (ppm): 3.96 (s, 6H, 2×OCH$_3$), 6.92~6.99 (d, 1H, 1×Ar—H), 7.45 (d, 1H, 1×Ar—H), 7.77 (d, 2H, 2×Ar—H), 7.82~7.91 (d, 2H, 2×Ar—H), 8.02 (s, 1H, imidazole-H).

ESI-MS m/z: 380.1[M+1]+, calculated: 380.1.

Example 77

Preparation of 4-(3,5-dimethoxyphenyl)-5-(3-amino-4-difluoromethoxyphenyl)imidazole (C153)

4-(3,5-Dimethoxyphenyl)-5-(3-amino-4-difluoromethoxyphenyl)imidazole was prepared according to the method as described in Example 33, as a yellow oil.

$^1$HNMR (CDCl$_3$) δ (ppm): 3.67 (s, 6H, 2×OCH$_3$), 4.26 (s, 1H, OCF$_2$H), 6.44~6.46 (t, 1H, Ar—H), 6.56~6.57 (d, 2H, 2×Ar—H), 6.75~6.77 (d, 2H, 2×Ar—H), 6.90~6.93 (d, 1H, 1×Ar—H), 7.98 (s, 1H, imidazole-H).

ESI-MS m/z: 362.1[M+1]+, calculated 362.1.

Example 78

Preparation of 4-(3,5-dimethoxy-4-aminophenyl)-5-(3-fluoro-4-methoxyphenyl)oxazole (CN01)

4-(3,5-Dimethoxy-4-aminophenyl)-5-(3-fluoro-4-methoxyphenyl)oxazole was prepared according to the method as described in Example 15, as a white solid, melting point: 100.8-102.6° C.

$^1$HNMR (DMSO) δ (ppm): 3.68 (m, 6H, 2×OCH3), 3.86 (m, 3H, 1×OCH3), 6.78 (S, 2H, 2×Ar—H), 7.38 (m, 3H, 3×Ar—H), 8.40 (s, 1H, oxazole-H).

ESI-MS m/z: 345.5 [M+1]+, calculated: 345.3.

Example 79

Preparation of 4-(3,5-dimethoxy-4-hydroxyphenyl)-5-(3-fluoro-4-methoxyphenyl)oxazole (CN03)

4-(3,5-Dimethoxy-4-hydroxyphenyl)-5-(3-fluoro-4-methoxyphenyl)oxazole was prepared according to the method as described in Example 15, as a white solid, melting point: 161.3-162.8° C.

$^1$HNMR (CDCl$_3$) δ (ppm): 3.84 (s, 6H, 2×OCH$_3$), 3.93 (s, 3H, 1×OCH$_3$), 5.68 (s, 1H, 1×OH), 6.89 (d, 3H, 3×Ar—H), 7.28-7.39 (d, 2H, 2×Ar—H), 7.92 (s, 1H, oxazole-H).

ESI-MS m/z: 346.2 [M+1]+, calculated: 346.1.

Example 80

Preparation of 4-(3,5-dimethoxy-4-bromophenyl)-5-(3-hydroxy-4-methoxyphenyl)oxazole (CN02)

4-(3,5-Dimethoxy-4-bromophenyl)-5-(3-hydroxy-4-methoxyphenyl)oxazole was prepared according to the method as described in Example 15, as a white solid, melting point: 184.7-187.0° C.

$^1$HNMR (CDCl$_3$) δ (ppm): 3.76 (s, 6H, 2×OCH$_3$), 3.92 (s, 3H, 1×OCH$_3$), 5.76 (s, 1H, 1×OH), 6.44 (s, 1H, 1×Ar—H), 6.85 (d, 3H, 3×Ar—H), 7.14 (d, 1H, 1×Ar—H), 7.91 (s, 1H, oxazole-H).

ESI-MS m/z: 406.1[M+1]+, calculated: 406.2.

Example 81

Preparation of 4-(3,5-dimethoxy-4-bromophenyl)-5-(3-amino-4-methoxyphenyl)oxazole (CN04)

4-(3,5-Dimethoxy-4-bromophenyl)-5-(3-amino-4-methoxyphenyl)oxazole was prepared according to the method as described in Example 15, as a white solid, melting point: 179.8-183.9° C.

$^1$HNMR (CDCl$_3$) δ (ppm): 3.84 (s, 6H, 2×OCH$_3$), 3.93 (s, 3H, 1×OCH$_3$), 6.89 (d, 3H, 3×Ar—H), 7.26-7.39 (d, 2H, 2×Ar—H), 7.92 (s, 1H, oxazole-H)

ESI-MS m/z: 405.1 [M+1]+, calculated: 405.0.

Example 82

Preparation of 4-(3,5-dimethoxy-4-hydroxyphenyl)-5-(3-amino-4-methoxyphenyl)oxazole (CN05)

4-(3,5-Dimethoxy-4-hydroxyphenyl)-5-(3-amino-4-methoxyphenyl)oxazole was prepared according to the method as described in Example 15, as a white solid, melting point: 101.2-102.0° C.

$^1$HNMR (CDCl$_3$) δ (ppm): 3.67-3.77 (s, 6H, 2×OCH$_3$), 3.99 (s, 3H, 1×OCH$_3$), 4.39 (s, 2H, 1×NH$_2$), 6.81 (s, 2H, 2×Ar—H), 6.81-7.06 (d, 3H, 3×Ar—H), 8.34 (s, 1H, oxazole-H).

ESI-MS m/z: 343.3 [M+1]+, calculated: 343.1.

Example 83

Preparation of 4-(3,5-dimethoxy-4-hydroxyphenyl)-5-(3-hydroxy-4-methoxyphenyl)oxazole (CN06)

4-(3,5-Dimethoxy-4-hydroxyphenyl)-5-(3-hydroxy-4-methoxyphenyl)oxazole was prepared according to the method as described in Example 15, as a white solid, melting point: 144.3-145.5° C.

$^1$HNMR (CDCl$_3$) δ (ppm): 3.83 (s, 6H, 2×OCH$_3$), 3.93 (s, 3H, 1×OCH$_3$), 5.62-5.71 (s, 2H, 2×OH), 6.87 (d, 1H, 1×Ar—H), 6.93 (S, 2H, 2×Ar—H), 7.14-7.26 (d, 2H, 2×Ar—H), 7.90 (s, 1H, oxazole-H).

ESI-MS m/z: 344.4 [M+1]+, Calculated: 344.1.

Example 84

Preparation of 4-(3,5-dimethoxy-4-nitrophenyl)-5-(3-hydroxy-4-methoxyphenyl)oxazole (CN07)

4-(3,5-Dimethoxy-4-nitrophenyl)-5-(3-hydroxy-4-methoxyphenyl)oxazole was prepared according to the method as described in Example 15, as a white solid, melting point: 186.2-188.4° C.

$^1$HNMR (CDCl$_3$) δ (ppm): 3.89 (s, 6H, 2×OCH$_3$), 3.95 (s, 3H, 1×OCH$_3$), 6.88-6.90 (d, 1H, 1×Ar—H), 7.02 (s, 2H, 2×Ar—H), 7.17-7.28 (d, 2H, 2×Ar—H), 7.94 (s, 1H, oxazole-H).

ESI-MS m/z: 373.5 [M+1]+, calculated: 373.1.

Example 85

Preparation of 4-(3,5-dimethoxy-4-aminophenyl)-5-(3-hydroxy-4-methoxyphenyl)oxazole (CN08)

4-(3,5-Dimethoxy-4-aminophenyl)-5-(3-hydroxy-4-methoxyphenyl)oxazole was prepared according to the method as described in Example 15, as a white solid, melting point: 126-129.6° C.

$^1$HNMR (CDCl$_3$) δ (ppm): 3.81 (s, 6H, 2×OCH$_3$), 3.95 (s, 3H, 1×OCH$_3$), 6.87-6.90 (d, 1H, 1×Ar—H), 7.00 (s, 2H, 2×Ar—H), 7.00-7.26 (d, 2H, Ar—H), 7.95 (s, 1H, oxazole-H).

ESI-MS m/z: 343.2 [M+1]⁺, calculated: 343.1.

Example 86

Preparation of 4-(3,5-dimethoxy-4-bromophenyl)-5-(3-hydroxy-4-methoxyphenyl) imidazole (CN11)

4-(3,5-Dimethoxy-4-bromophenyl)-5-(3-hydroxy-4-methoxyphenyl) imidazole was prepared according to the method as described in Example 33, as a white solid, melting point: 184.7-187.0° C.

¹HNMR (CDCl₃) δ (ppm): 3.76 (s, 6H, 2×OCH₃), 3.92 (s, 3H, 1×OCH₃), 5.76 (s, 1H, 1×OH), 6.78-6.80 (d, 1H, 1×Ar—H), 6.84 (s, 2H, 2×Ar—H), 7.14-7.26 (d, 2H, 2×Ar—H), 7.91 (s, 1H, imidazole-H).

ESI-MS m/z: 405.3 [M+1]⁺, calculated: 405.2.

Example 87

Preparation of 4-(3,5-dimethoxy-4-hydroxyphenyl)-5-(3-fluoro-4-methoxyphenyl) imidazole (CN12)

4-(3,5-Dimethoxy-4-hydroxyphenyl)-5-(3-fluoro-4-methoxyphenyl) imidazole was prepared according to the method as described in Example 33, as a white solid, melting point: 124.7-127.0° C.

¹HNMR (CDCl₃) δ (ppm): 3.90 (s, 6H, 2×OCH₃), 4.12 (s, 3H, 1×OCH₃), 5.68 (s, 1H, 1×OH), 6.71-6.80 (d, 1H, 1×Ar—H), 6.89 (s, 2H, 2×Ar—H), 7.12-7.39 (d, 2H, 2×Ar—H), 7.99 (s, 1H, imidazole-H).

ESI-MS m/z: 345.3 [M+1]⁺, calculated: 345.1.

Example 88

Preparation of 4-(3,5-dimethoxy-4-bromophenyl)-5-(3-amino-4-methoxyphenyl)imidazole (CN13)

4-(3,5-Dimethoxy-4-bromophenyl)-5-(3-amino-4-methoxyphenyl) imidazole was prepared according to the method as described in Example 33, as a white solid, melting point: 159.7-162.0° C.

¹HNMR (CDCl₃) δ (ppm): 3.99 (s, 6H, 2×OCH₃), 4.32 (s, 3H, 1×OCH₃), 6.71-6.79 (d, 1H, 1×Ar—H), 6.90 (s, 2H, 2×Ar—H), 7.33-7.41 (d, 2H, 2×Ar—H), (s, 1H, imidazole-H).

ESI-MS m/z: 404.1 [M+1]⁺, calculated: 404.0.

Example 89

Preparation of 4-(3,5-dimethoxy-4-hydroxyphenyl)-5-(3-amino-4-methoxyphenyl)imidazole (CN14)

4-(3,5-Dimethoxy-4-hydroxyphenyl)-5-(3-amino-4-methoxyphenyl) imidazole was prepared according to the method as described in Example 33, as a white solid, melting point: 148.5-149.9° C.

¹HNMR (CDCl₃) δ (ppm): 3.87 (s, 6H, 2×OCH₃), 4.11 (s, 3H, 1×OCH₃), 6.73-6.85 (d, 1H, 1×Ar—H), 6.93 (s, 2H, 2×Ar—H), 7.12-7.39 (d, 2H, 2×Ar—H), 8.01 (s, 1H, imidazole-H).

ESI-MS m/z: 342.2 [M+1]⁺, calculated: 342.1.

Example 90

Preparation of 4-(3,5-dimethoxy-4-hydroxyphenyl)-5-(3-hydroxy-4-methoxyphenyl)imidazole (CN15)

4-(3,5-Dimethoxy-4-hydroxyphenyl)-5-(3-hydroxy-4-methoxyphenyl) imidazole was prepared according to the method as described in Example 33, as a white solid, melting point: 171.5-173.0° C.

¹HNMR (CDCl₃) δ (ppm): 3.90 (s, 6H, 2×OCH₃), 4.01 (s, 3H, 1×OCH₃), 6.78-6.90 (d, 1H, 1×Ar—H), 6.98 (s, 2H, 2×Ar—H), 7.32-7.39 (d, 2H, 2×Ar—H), 8.12 (s, 1H, imidazole-H).

ESI-MS m/z: 343.1 [M+1]⁺, calculated: 343.1.

Example 91

Preparation of 4-(3,5-dimethoxy-4-nitrophenyl)-5-(3-hydroxy-4-methoxyphenyl)imidazole (CN16)

4-(3,5-Dimethoxy-4-nitrophenyl)-5-(3-hydroxy-4-methoxyphenyl) imidazole was prepared according to the method as described in Example 33, as a white solid, melting point: 147.7-149.0° C.

¹HNMR (CDCl₃) δ (ppm): 3.98 (s, 6H, 2×OCH₃), 4.13 (s, 3H, 1×OCH₃), 6.73-6.82 (d, 1H, 1×Ar—H), 6.95 (s, 2H, 2×Ar—H), 7.21-7.32 (d, 2H, 2×Ar—H), 7.89 (s, 1H, imidazole-H).

ESI-MS m/z: 372.2 [M+1]⁺, calculated: 372.1.

Example 92

Preparation of 4-(3,5-dimethoxy-4-aminophenyl)-5-(3-hydroxy-4-methoxyphenyl) imidazole (CN17)

4-(3,5-Dimethoxy-4-aminophenyl)-5-(3-hydroxy-4-methoxyphenyl)imidazole was prepared according to the method as described in Example 33, as a white solid, melting point: 141.8-143.7° C.

¹HNMR (CDCl₃) δ (ppm): 3.77 (s, 6H, 2×OCH₃), 4.01 (s, 3H, 1×OCH₃), 6.62-6.70 (d, 1H, 1×Ar—H), 6.83 (s, 2H, 2×Ar—H), 7.02-7.19 (d, 2H, 2×Ar—H), 7.95 (s, 1H, imidazole-H).

ESI-MS m/z: 342.3 [M+1]⁺, calculated: 342.2.

Example 93

Preparation of 4-(3,5-dimethoxy-4-aminophenyl)-5-(3-amino-4-methoxyphenyl) imidazole (CN19)

4-(3,5-Dimethoxy-4-aminophenyl)-5-(3-amino-4-methoxyphenyl) imidazole was prepared according to the method as described in Example 33, as a white solid, melting point: 139.7-142.1° C.

¹HNMR (CDCl₃) δ (ppm): 3.77 (s, 6H, 2×OCH₃), 4.07 (s, 3H, 1×OCH₃), 6.62-6.70 (d, 1H, 1×Ar—H), 6.82 (s, 2H, 2×Ar—H), 7.32-7.44 (d, 2H, 1×Ar—H), 8.04 (s, 1H, imidazole-H).

ESI-MS m/z: 341.3[M+1]$^+$, calculated: 341.1.

Example 94

Preparation of 4-(3,5-dimethoxy-4-fluorophenyl)-5-(3-amino-4-methoxyphenyl)oxazole (CN20)

4-(3,5-Dimethoxy-4-fluorophenyl)-5-(3-amino-4-methoxyphenyl)oxazole was prepared according to the method as described in Example 15, as a white solid, melting point: 139.7-142.1° C.

$^1$HNMR (CDCl$_3$) δ (ppm): 3.69 (s, 6H, 2×OCH$_3$), 4.01 (s, 3H, 1×OCH$_3$), 6.82-6.90 (d, 1H, 1×Ar—H), 6.95 (s, 2H, 2×Ar—H), 7.02-7.14 (d, 2H, 2×Ar—H), 8.55 (s, 1H, oxazole-H).

ESI-MS m/z: 345.1 [M+1]$^+$, calculated: 345.1.

Example 95

Preparation of 4-(3,5-dimethoxy-4-chlorophenyl)-5-(3-amino-4-methoxyphenyl)oxazole (CN21)

4-(3,5-Dimethoxy-4-chlorophenyl)-5-(3-amino-4-methoxyphenyl)oxazole was prepared according to the method as described in Example 15, as a white solid, melting point: 146.2-148.1° C.

$^1$HNMR (CDCl$_3$) δ (ppm): 3.96 (s, 6H, 2×OCH$_3$), 4.16 (s, 3H, 1×OCH$_3$), 6.72-6.80 (d, 1H, 1×Ar—H), 6.89 (s, 2H, 2×Ar—H), 7.12-7.33 (d, 2H, 2×Ar—H), 8.24 (s, 1H, oxazole-H).

ESI-MS m/z: 361.3 [M+1]$^+$, calculated: 361.2.

Example 96

Preparation of 4-(3,5-dimethoxy-4-trifluoromethoxyphenyl)-5-(3-amino-4-methoxyphenyl)oxazole (CN23)

4-(3,5-Dimethoxy-4-trifluoromethoxyphenyl)-5-(3-amino-4-methoxyphenyl)oxazole was prepared according to the method as described in Example 15, as a white solid, melting point: 167.9-170.2° C.

$^1$HNMR (CDCl$_3$) δ (ppm): 3.93 (s, 6H, 2×OCH$_3$), 4.05 (s, 3H, 1×OCH$_3$), 6.82-6.90 (d, 1H, 1×Ar—H), 6.95 (s, 2H, 2×Ar—H), 7.21-7.34 (d, 2H, 2×Ar—H), 8.26 (s, 1H, oxazole-H).

ESI-MS m/z: 411.3 [M+1]$^+$, calculated: 411.1.

Example 97

Preparation of 4-(3,5-dimethoxy-4-methylaminophenyl)-5-(3-amino-4-methoxyphenyl)oxazole (CN24)

4-(3,5-Dimethoxy-4-aminophenyl)-5-(3-amino-4-methoxyphenyl)oxazole was prepared according to the method as described in Example 15, as a white solid, melting point: 134.3.7-137.1° C.

$^1$HNMR (CDCl$_3$) δ (ppm): 2.59-2.80 (s, 3H, 1×NCH$_3$) 3.89 (s, 6H, 2×OCH$_3$), 4.15 (s, 3H, 1×OCH$_3$), 6.93 (s, 3H, 3×Ar—H), 7.21-7.35 (d, 2H, 2×Ar—H), 8.12 (s, 1H, oxazole-H).

ESI-MS m/z: 35.2 [M+1]$^+$, calculated: 35.1.

Example 98

Preparation of 4-(3,5-dimethoxy-4-aminophenyl)-5-(3-fluoro-4-methoxyphenyl) imidazole (CN10)

4-(3,5-Dimethoxy-4-aminophenyl)-5-(3-fluoro-4-methoxyphenyl) imidazole was prepared according to the method as described in Example 33, as a white solid, melting point: 100.8-102.6° C.

$^1$HNMR (CDCl$_3$) δ (ppm): 3.68 (s, 6H, 2×OCH$_3$), 3.86 (s, 3H, 1×OCH$_3$), 4.42 (s, 2H, 1×NH$_2$), 6.78 (S, 2H, 2×Ar—H), 7.38 (d, 3H, 3×Ar—H), 8.40 (s, 1H, imidazole-H).

ESI-MS m/z: 344.3[M+1]$^+$, calculated: 344.1.

Example 99

Preparation of 4-(3,5-dimethoxyphenyl)-5-(3-hydroxy-4-methoxyphenyl)oxazole phosphate, disodium salt (C110P)

Under ice-water cooling, 1 g C110 (3.06 mmol) was dissolved in 20 ml dichloromethane, and 1 ml phosphorus oxychloride was added, and then 1 ml triethylamine was slowly added dropwise. Subsequently, the mixture was warmed to room temperature, and reacted for 2 hours. The reaction solution was concentrated to dryness under reduced pressure, and then basified with aqueous solution of sodium hydroxide. The solution was stirred at room temperature for 2 hours, and 20 ml acetone was added to precipitate a white solid. The product was filtered and dried to give 4-(3,5-dimethoxyphenyl)-5-(3-hydroxy-4-methoxyphenyl)oxazole phosphate disodium salt as a white solid, melting point: 196.2~197.5° C.

$^1$HNMR (DMSO) δ (ppm): 3.85 (s, 3H, OCH$_3$), 4.08 (s, 6H, 2×OCH$_3$), 6.23~6.45 (m, 1H, O—H), 6.85~6.92 (d, 2H, 2×Ar—H), 7.55 (d, 1H, Ar—H), 7.81 (d, 2H, 2×Ar—H), 7.90~7.99 (d, 1H, Ar—H), 8.15 (s, 1H, oxazole-H).

$^{31}$P NMR (DMSO) δ (ppm): −3.679 (s, 1P).

Example 100

Preparation of 4-(3,5-dimethoxyphenyl)-5-(3-hydroxy-4-methoxyphenyl)oxazole phosphate tromethamine (CHOP.tris)

4-(3,5-Dimethoxyphenyl)-5-(3-hydroxy-4-methoxyphenyl)oxazolephosphate ester (1 g, 2.45 mmol)) was dissolved in isopropanol, and an equimolar amount of tromethamine was added. The mixture was stirred for 18 hours, cooled with an ice bath, and filtered to give the desired compound, as a white solid, melting point: 226.1~228.0° C.

$^1$HNMR (DMSO) δ (ppm): 3.45 (s, 6H, OCH$_2$), 3.92 (s, 3H, OCH$_3$), 4.01 (s, 6H, 2×OCH$_3$), 5.19 (t, 3H, OH), 6.33~6.49 (m, 1H, O—H), 6.79~6.88 (d, 2H, 2×Ar—H), 7.45 (d, 1H, Ar—H), 7.74 (d, 2H, 2×Ar—H), 7.89~7.97 (d, 1H, Ar—H), 8.09 (s, 1H, oxazole-H).

Example 101

Preparation of 4-(3,5-dimethoxyphenyl)-5-(3-hydroxy-4-methoxyphenyl)imidazole phosphate, disodium salt 4-(3,5-Dimethoxyphenyl)-5-(3-hydroxy-4-methoxyphenyl)imidazole phosphate, disodium salt was prepared according to the methods as described above, as a white solid, melting point: 169.7-172.1° C.

$^1$HNMR (DMSO) δ (ppm): 3.92 (s, 3H, OCH$_3$), 4.21 (s, 6H, 2×OCH$_3$), 6.47~6.56 (m, 1H, O—H), 6.77~6.89 (d, 2H, 2×Ar—H), 7.63 (d, 1H, Ar—H), 7.89 (d, 2H, 2×Ar—H), 7.55~7.67 (d, 1H, Ar—H), 8.32 (s, 1H, imidazole-H).

$^{31}$PNMR (DMSO) δ (ppm): −3.545 (s, 1P).

Example 102

Preparation of 4-(3,4,5-trimethoxyphenyl)-5-(3-fluoro-4-methoxyphenyl)oxazole (C094)

4-(3,4,5-Trimethoxyphenyl)-5-(3-fluoro-4-methoxyphenyl)oxazole was prepared according to the method as described in Example 15, as a white solid, melting point: 139~140° C.

$^1$HNMR (CDCl$_3$) δ (ppm): 3.80 (s, 6H, 2×OCH$_3$), 3.89 (s, 3H, 1×OCH$_3$), 3.93 (s, 3H, 1×OCH$_3$), 6.90 (s, 2H, 2×Ar—H), 6.96~6.99 (t, 1H, 1×Ar—H), 7.38~7.43 (m, 2H, 2×Ar—H), 7.92 (s, 1H, oxazole-H).

ESI-MS m/z: 360.1[M+1]$^+$, calculated: 360.4.

Example 103

Preparation of 5-(3,5-dimethoxyphenyl)-4-(3-hydroxy-4-methoxyphenyl)-1-methylimidazole (C126)

5-(3,5-Dimethoxyphenyl)-4-(3-hydroxy-4-methoxyphenyl)-1-methylimidazole was prepared according to the method as described in Example 30, as a white solid, melting point: 198.5~200.4° C.

$^1$HNMR (CDCl$_3$) δ (ppm): 3.59~3.66 (s, 3H, 1×N—CH$_3$), 3.70 (s, 6H, 2×OCH$_3$), 4.11~4.13 (s, 3H, 1×OCH$_3$), 6.33~6.34 (d, 1H, 1×Ar—H), 6.77~6.78 (d, 2H, 2×Ar—H), 6.81~6.85 (m, 1H, 1×Ar—H), 6.94~6.97 (m, 2H, 2×Ar—H), 8.47 (s, 1H, imidazole-H).

ESI-MS m/z: 341.4 [M+1]$^+$, Calculated: 341.4.

Example 104

Preparation of 4-(3,5-dimethoxyphenyl)-5-(3-hydroxy-4-methoxyphenyl)-1-(3,4,5-trimethoxyphenyl)imidazole (C101)

4-(3,5-Dimethoxyphenyl)-5-(3-hydroxy-4-methoxyphenyl)-1-(3,4,5-trimethoxyphenyl)imidazole was prepared according to the method as described in Example 1, as light yellow solid, melting point: 110~111.3° C.

$^1$HNMR (CDCl$_3$) δ (ppm): 3.66 (s, 6H, 2×OCH$_3$), 3.68 (s, 6H, 2×OCH$_3$), 3.83 (s, 3H, OCH$_3$), 3.87 (s, 3H, OCH$_3$), 6.28 (s, 2H, 2×Ar—H), 6.34 (t, 1H, Ar—H), 6.75~6.77 (m, 2H, 2×Ar—H), 6.79~6.80 (m, 1H, Ar—H), 6.83 (s, 1H, Ar—H), 7.27~7.29 (m, 1H, 1×Ar—H), 7.74 (s, 1H, imidazole-H).

ESI-MS m/z: 493.2 [M+1]$^+$, calculated: 493.5.

Example 105

Assay of Anti-Tumor Activity of Some Exemplified Compounds

The cells were digested and counted. The cell suspension was prepared in a concentration of 5×10$^4$ cells/ml. 100 μL of the cell suspension per well was added into 96-well plates (5×10$^3$ cells per well). The 96-well plates were placed in a 5% CO$_2$ incubator at 37° C. for 24 hours. The drugs were diluted with the complete medium to the desired concentrations. 100 μL of the corresponding drug-containing medium was added into each well. Negative control group, vehicle control group and positive control group were set. The 96-well plates were placed in 5% CO$_2$ incubator at 37° C. for 72 hours. The 96-well plates were subjected to a MTT assay, and measured OD value at λ=490 nm. The measurement procedure comprises adding 20 μL MTT (5 mg/ml) for each well, incubating for 4 hours in an incubator, discarding the medium, dissolving by adding 150 μL DMSO into each well, mixing uniformly by rocking gently for 10 minutes on a shaker, reading OD value of each well in a microplate reader at λ=490 nm. The inhibition rate was calculated, the results were recorded, and the anti-tumor activity was assessed. The results are shown in Table 1.

TABLE 1

Anti-tumor activity of some compounds

| Tested compounds | Cell strains IC$_{50}$ nM | | | | |
|---|---|---|---|---|---|
| | K562 | MCF-7 | HCT-116 | NCI-H460 | DU-145 |
| C087 | 4.6 | 6.2 | 77 | 153 | >300 |
| C123 | 7.2 | 1.2 | 189 | 126 | >300 |
| C128 | 1.9 | 1 | 110 | 92 | not determined |
| C106 | 3.2 | 7.3 | 136 | >300 | 92.3 |
| C130 | 23 | 162 | 25 | 350 | 76.3 |
| C105 | 8.9 | 21 | 151 | 21 | not determined |
| C110 | 49 | 210 | 71 | 33 | 2.5 |
| C115 | 5.7 | 101 | 335 | 52 | >300 |
| C117 | 8.5 | 88.9 | >300 | 10.2 | 130 |
| C123 | 7.2 | 1.2 | >300 | 16.8 | >300 |
| C124 | 6.4 | 4.3 | 33 | >300 | 280 |
| C130 | 21.3 | 56 | 25 | >300 | 210.3 |
| C132 | 4.5 | 7.8 | 52 | 90.1 | >300 |
| C135 | 6.9 | 5.6 | 68 | 76.3 | 161 |
| C118 | 2.804 | 46.3 | 40.5 | 14.3 | not determined |
| C238 | 11.2 | 6.1 | 230 | >300 | 150 |
| C253 | 310 | 6.4 | 121 | 26.4 | 76.2 |
| C256 | 7.6 | not determined | 460 | >300 | 10.3 |
| C248 | 11.2 | 6.9 | 312 | 10.3 | >300 |
| C142 | 4.2 | 11.3 | 416 | 62 | 4.1 |
| C146 | 6.1 | 9.3 | 289 | not determined | >300 |
| C147 | 7.6 | 8.9 | >300 | 89.3 | 123.0 |
| C152 | 6.8 | 10.2 | 34 | >300 | not determined |
| CA4 | 5.2 | 5.5 | 43 | 5.6 | 7.2 |

Example 106

Assay of Inhibitory Activity of the Compounds on Tubulin Polymerization

The compounds were formulated into six different concentrations (0.03, 0.3, 0.9, 3, 9, 30 μM). The tubulin polymerization assay kit (Cat. # BK011P, Cytoskeleton) was used for testing. The samples were incubated at 37° C. for 60 minutes, and then fluorescence was collected using Gemini EM Fluorescence Microplate Reader collected at 410-460 nm. Vmax was calculated using SOFTMAX® PRO microplate data acquisition & analysis software. The tubulin inhibition (IC$_{50}$) of the compound was calculated using GRAPHPAD PRISM® v5.01 graphing and statistics software. The results for some of the compounds are shown in Table 2.

TABLE 2

Inhibitory activity of some compounds on tubulin polymerization

| Tested compounds | IC$_{50}$ uM |
|---|---|
| CA4 | 0.76 |
| C110 | 0.47 |
| C115 | 0.46 |
| C116 | 0.53 |
| C118 | 0.49 |
| C121 | 2.35 |
| C123 | 0.66 |
| C124 | 1.04 |
| C128 | 0.59 |
| C129 | 0.66 |
| C256 | 1.57 |
| C264 | 0.86 |

Example 107

Study of the Pharmacokinetics of Compound C128 Liposome

1. Formulation

C128 liposomes: (The liposome was prepared according to the conventional method in the pharmaceutical field, particle size 62.6 nm, polydispersity 0.532).

2. Experimental Methods

SD male rats, with average weight of 200 g.

2.1 Determination of the Concentration of Compound C128 in the Biological Samples 2.1.1 Chromatographic Conditions Chromatographic conditions: LC-20A high performance liquid chromatography, SPD-20A variable wavelength UV detector (Shimadzu Corporation, Japan); C18 pre-column; mobile phase: methanol/water (65/35, v/v); flow rate 1 mL/min; detection wavelength 283 nm; column temperature 40° C.

2.1.2 Processing of the Biological Samples

The blood was collected from the orbital sinus of rats and centrifuged for 10 minutes at 3000 r/min, and the plasma was separated. 200 μL of the plasma was accurately sampled, and placed in 1.5 mL EP tube. 600 μL acetonitrile was added. The tube was vortexed for 3 minutes, and centrifuged for 10 minutes at 16000 r/min. 20 μL supernatant was taken for injection of HPLC determination. Chromatograms and peak area were recorded.

2.1.3 Preparation of Standard Curve of the Biological Samples

Blank plasma (280 μL) was accurately pipetted, and 20 μL of standard solutions of different concentrations of the drug was added to obtain the biological samples of different concentrations of the drug. The samples were treated and measured according to the aforementioned "Processing of the biological samples". The chromatogram and the peak area were recorded. Linear regression was made by peak area A v.s concentration C (μg/mL) to obtain the standard working curve of Compound C128 in the biological samples.

2.2 Dosing Regimen

Three male rats were used, and administered via tail vein injection at a dose of 10 mg/kg. The blood was taken via the orbital sinus after administration of 5 min, 15 min, 30 min, 1 h, 2 h, 4 h, 6 h, 8 h, 10 h, respectively. The samples were treated and measured according to the aforementioned "Processing of the biological samples". The chromatogram and the peak area were recorded. The measured amount, namely, the drug concentration in plasma, was calculated by putting the peak area of the drug into the standard working curve equation.

2.3 Processing of the Experimental Data

The time curve of the drug in plasma was drawn—the area under the plasma drug concentration-time curve (AUC) was calculated by the Log trapezoidal method.

2.4 Results and Discussion 2.4.1 Establishment of Rat Plasma Analysis Method

The chromatogram of the plasma sample consisting of blank rat plasma added with the drug was established. The drug retention time was about 10.8 min, and the peak shape was perfect. The natural substances in the plasma did not substantially interfere with the determination of drugs. Under such liquid phase condition, the plasma drug concentration standard curve ranged between 0.050 μg/mL and 8.000 μg/mL. Regression coefficient (R2) was greater than 0.999, indicating a good linear relationship.

2.4.2 Experimental Data and Fitting Results

The plasma concentration—time curve of Compound C128 refers to FIG. 1.

The fitting results using non-compartmental model analysis are shown in Table 3 below.

TABLE 3

Non-compartmental model analysis of Compound C128

| Parameter | Unit | Liposomes |
|---|---|---|
| Lambda$_z$ | 1/h | 0.833 |
| t$_{1/2}$ | h | 0.834 |
| T$_{max}$ | h | 0.083 |
| C$_{max}$ | μg/ml | 14.180 |
| C$_0$ | μg/ml | 20.421 |
| C$_{last\_obs}$/C$_{max}$ | | 0.029 |
| AUC$_{0-t}$ | μg/ml*h | 7.284 |
| AUC$_{0-inf\_obs}$ | μg/ml*h | 7.771 |
| AUC$_{0-t/0-inf\_obs}$ | | 0.936 |
| AUMC$_{0-inf\_obs}$ | μg/ml*h$^2$ | 7.569 |
| MRT$_{0-inf\_obs}$ | h | 0.982 |
| Vz$_{\_obs}$ | (mg/kg)/(μg/ml) | 1.573 |
| Cl$_{\_obs}$ | (mg/kg)/(μg/ml)/h | 1.302 |
| Vss$_{\_obs}$ | (mg/kg)/(μg/ml)/h | 1.288 |

What is claimed is:

1. A compound of formula I,

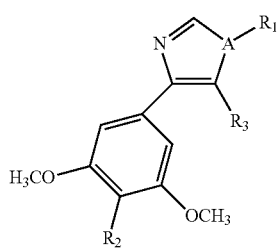

(I)

or a phosphate ester, a sulfonate ester, a pharmaceutically acceptable salt, a glycoside derivative or a solvate thereof, wherein A is N, O or S;

when A is O or S, R$_1$ is absent;

when A is N, R$_1$ is H, CH$_3$, C$_4$H$_9$,

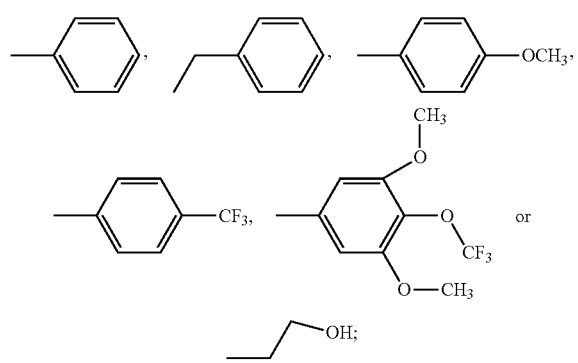
R$_2$ is H, CF$_3$, OCF$_3$, OCHF$_2$ or —NHCH$_3$; and
R$_3$ is selected from the group consisting of:
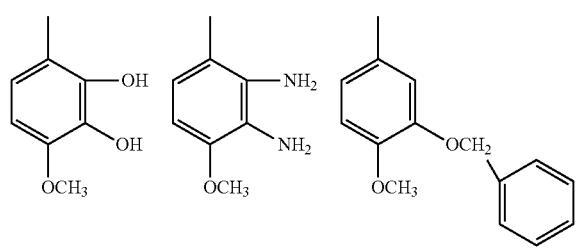
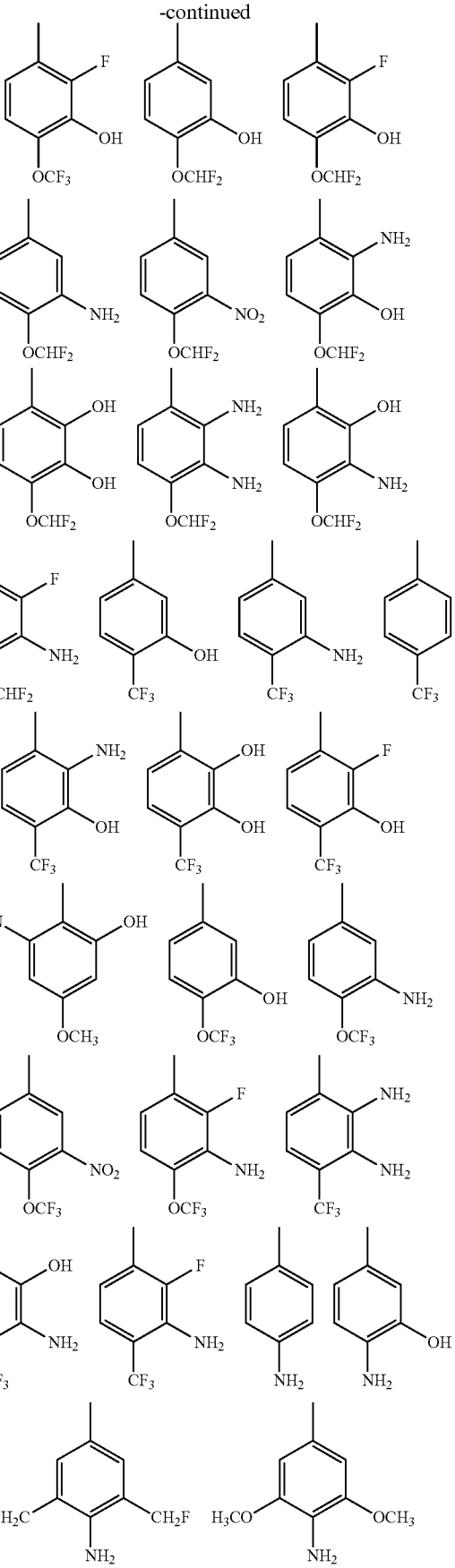

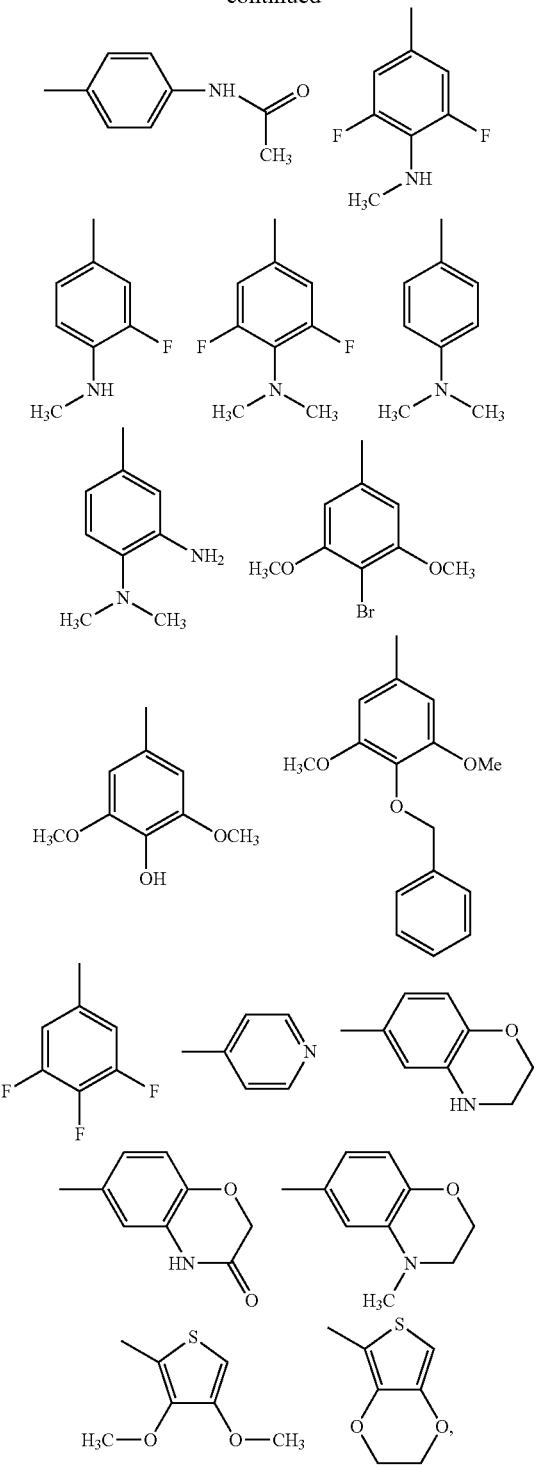
with the proviso that the following compounds are excluded:
1) when A is N:
   $R_1$ is $CH_3$, $R_2$ is H, and $R_3$ is 4-$N(CH_3)_2C_6H_4$, 3-F-4-$(OCH_3)C_6H_3$, 3-$(NH_2)$-4-$(OCH_3)C_6H_3$ or 3,5-$(OCH_3)_2$-4-Br—$C_6H_2$;
   $R_1$ is $C_4H_9$, $C_6H_5$ or 4-methoxyphenyl, $R_2$ is H, and $R_3$ is 4-$N(CH_3)_2C_6H_4$; and
2) when A is O:
   $R_2$ is H, and $R_3$ is 3,5-$(OCH_3)_2$-4-Br—$C_6H_2$.
2. The compound of claim 1, wherein $R_3$ is selected from the group consisting of:
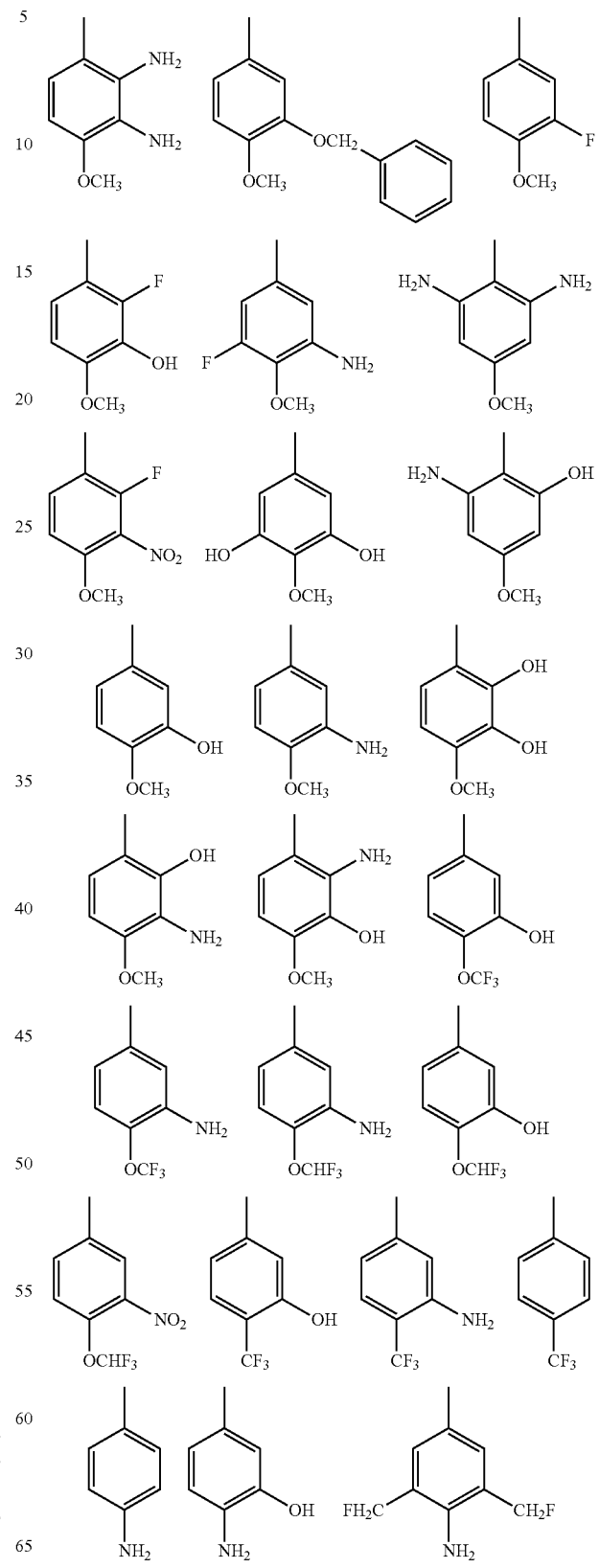

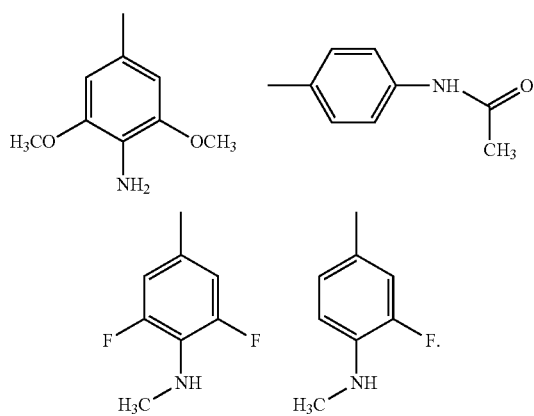

3. The compound of claim 1, wherein:
when A is N, $R_1$ is H,

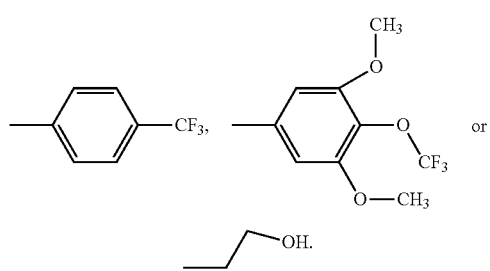

4. The compound of claim 1, wherein:
A and $R_1$ together are O, NH or —$NCH_3$;
$R_2$ is H, $OCF_3$ or $OCHF_2$; and
$R_3$ is selected from the group consisting of:

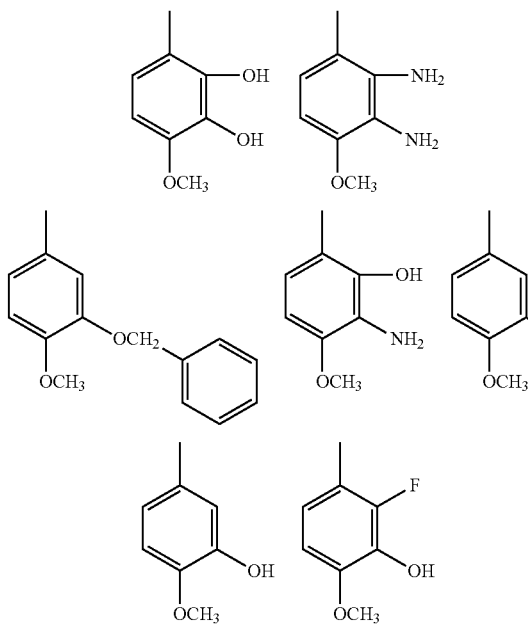

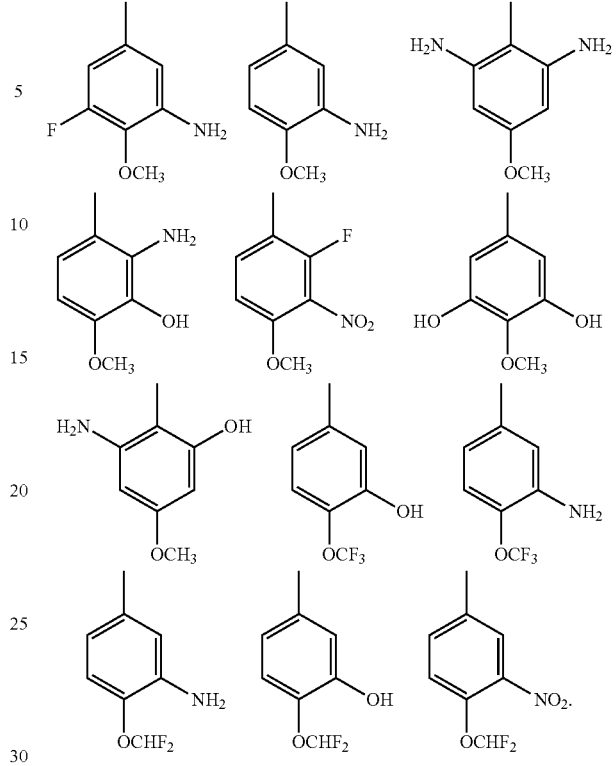

5. A compound of claim 1, selected from:
5-(3-hydroxy-4-methoxyphenyl)-4-(3,5-dimethoxyphenyl)-1-(4-methoxyphenyl)imidazole;
5-(4-dimethylaminophenyl)-4-(3,5-dimethoxyphenyl)-1-(4-trifluoromethylphenyl)imidazole;
5-(3-hydroxy-4-methoxyphenyl)-4-(3,5-dimethoxyphenyl)-1-(4-trifluoromethylphenyl)imidazole;
5-(3-fluoro-4-methoxyphenyl)-4-(3,5-dimethoxyphenyl)-1-(3,4,5-trimethoxyphenyl)imidazole;
5-(4-dimethylaminophenyl)-4-(3,5-dimethoxyphenyl)-1-(3,4,5-trimethoxyphenyl)imidazole;
4-(3,5-dimethoxyphenyl)-5-(3-hydroxy-4-methoxyphenyl)oxazole;
4-(3,5-dimethoxyphenyl)-5-(4-aminophenyl)oxazole;
4-(3,5-dimethoxyphenyl)-5-(3-amino-4-dimethylaminophenyl)oxazole;
4-(3,5-dimethoxyphenyl)-5-(3-amino-4-methoxy-5-fluorophenyl)oxazole;
4-(3,5-dimethoxyphenyl)-5-(3-amino-4-methoxyphenyl)oxazole;
4-(3,5-dimethoxyphenyl)-5-(2,3-dihydroxy-4-methoxyphenyl)oxazole;
4-(3,5-dimethoxyphenyl)-5-(2-fluoro-3-hydroxy-4-methoxyphenyl)oxazole;
4-(3,5-dimethoxyphenyl)-5-(2,3-diamino-4-methoxyphenyl)oxazole;
4-(3,5-dimethoxyphenyl)-5-(2-amino-3-hydroxy-4-methoxyphenyl)oxazole;
4-(3,5-dimethoxyphenyl)-5-(3-amino-4-trifluoromethoxyphenyl)oxazole;
4-(3,5-dimethoxyphenyl)-5-(3-amino-4-difluoromethoxyphenyl)oxazole;
4-(3,5-dimethoxyphenyl)-5-(3-amino-4-trifluoromethoxyphenyl)-1-methylimidazole;
4-(3,5-dimethoxyphenyl)-5-(3-amino-4-difluoromethoxyphenyl)-1-methylimidazole;

4-(3,5-dimethoxyphenyl)-5-(2-fluoro-3-amino-4-methoxyphenyl)-1-methylimidazole;
4-(3,5-dimethoxyphenyl)-5-(3-hydroxy-4-methoxyphenyl)imidazole;
4-(3,5-dimethoxyphenyl)-5-(3-fluoro-4-methoxyphenyl)imidazole;
4-(3,5-dimethoxyphenyl)-5-(3-amino-4-methoxyphenyl)imidazole;
4-(3,5-dimethoxyphenyl)-5-(4-dimethylaminophenyl)imidazole;
N-methyl-4-(3,5-dimethoxyphenyl)-5-[(3,4-ethylenedioxyl)thienyl]imidazole;
N-methyl-4-(3,5-dimethoxyphenyl)-5-[6-(3-oxobenzomorpholinyl)]imidazole;
4-(3,5-dimethoxyphenyl)-5-[6-(3-oxobenzomorpholinyl)]oxazole;
N-methyl-4-(3,5-dimethoxyphenyl)-5-(6-benzomorpholinyl)-imidazole;
4-(3,5-dimethoxyphenyl)-5-(6-benzomorpholinyl)oxazole;
N-hydroxyethyl-4-(3,5-dimethoxyphenyl)-5-(3-fluoro-4-methoxyphenyl)imidazole;
N-hydroxyethyl-4-(3,5-dimethoxyphenyl)-5-[(3,4-ethylenedioxyl)thienyl]imidazole;
N-benzyl-4-(3,5-dimethoxyphenyl)-5-[(3,4-ethylenedioxyl)thienyl]imidazole;
N-methyl-4-(3,5-dimethoxyphenyl)-5-(3,4,5-trifluorophenyl)imidazole;
N-methyl-4-(3,5-dimethoxyphenyl)-5-(3,5-difluoro-4-methylaminophenyl)imidazole;
4-(3,5-dimethoxyphenyl)-5-(3-fluoro-4-methylaminophenyl)oxazole;
N-methyl-4-(3,5-dimethoxyphenyl)-5-[6-benzo(N-methylmorpholine)]imidazole;
4-(3,5-dimethoxyphenyl)-5-[6-benzo(N-methylmorpholine)]oxazole;
4-(3,5-dimethoxyphenyl)-5-(3-fluoro-4-methylaminophenyl)imidazole;
4-(3,5-dimethoxyphenyl)-5-(2-hydroxy-3-amino-4-methoxyphenyl)oxazole;
4-(3,5-dimethoxyphenyl)-5-(3-hydroxy-4-trifluoromethoxyphenyl)oxazole;
4-(3,5-dimethoxyphenyl)-5-(3-hydroxy-4-difluoromethoxyphenyl)oxazole;
4-(3,5-dimethoxyphenyl)-5-(2-hydroxy-3-hydroxy-4-methoxyphenyl)imidazole;
4-(3,5-dimethoxyphenyl)-5-(2-amino-3-amino-4-methoxyphenyl)imidazole;
4-(3,5-dimethoxyphenyl)-5-(2-hydroxy-3-amino-4-methoxyphenyl)imidazole;
4-(3,5-dimethoxyphenyl)-5-(2-amino-3-hydroxy-4-methoxyphenyl)imidazole;
4-(3,5-dimethoxyphenyl)-5-(2-fluoro-3-hydroxy-4-methoxyphenyl)imidazole;
4-(3,5-dimethoxyphenyl)-5-(2-fluoro-3-amino-4-methoxyphenyl)imidazole;
4-(3,5-dimethoxyphenyl)-5-(3-hydroxy-4-trifluoromethoxyphenyl)imidazole;
4-(3,5-dimethoxyphenyl)-5-(3-hydroxy-4-difluoromethoxyphenyl) imidazole;
4-(3,5-dimethoxyphenyl)-5-(3-amino-4-trifluoromethoxyphenyl)imidazole;
4-(3,5-dimethoxyphenyl)-5-(3-amino-4-difluoromethoxyphenyl)imidazole;
4-(3,5-dimethoxy-4-trifluoromethoxyphenyl)-5-(3-amino-4-methoxyphenyl)oxazole;
4-(3,5-dimethoxy-4-methylaminophenyl)-5-(3-amino-4-methoxyphenyl)oxazole;
4-(3,5-dimethoxyphenyl)-5-(3-hydroxy-4-methoxyphenyl)oxazole phosphate, disodium salt;
4-(3,5-dimethoxyphenyl)-5-(3-hydroxy-4-methoxyphenyl)oxazole phosphate tromethamine;
4-(3,5-dimethoxyphenyl)-5-(3-hydroxy-4-methoxyphenyl)imidazole phosphate, disodium salt;
and
4-(3,5-dimethoxyphenyl)-5-(3-hydroxy-4-methoxyphenyl)-1-(3,4,5-trimethoxyphenyl) imidazole;
or a phosphate ester, a sulfonate ester, a pharmaceutically acceptable salt, a glycoside derivative or a solvate thereof.

6. A compound of claim 1, wherein the pharmaceutically acceptable salt is hydrochloride, phosphate, nitrate, sulfate, citrate, sulfonate or amino acid salt.

7. A compound of claim 1, wherein the pharmaceutically acceptable salt is alkali metal salt, alkaline-earth metal salt or tromethamine salt of the phosphate ester or sulfonate ester of the compound of formula I.

8. A pharmaceutical composition comprising the compound of claim 1, or a phosphate ester, a sulfonate ester, a pharmaceutically acceptable salt, a glycoside derivative, or a solvate thereof.

9. The compound of claim 2, wherein:
when A is N, $R_1$ is H,

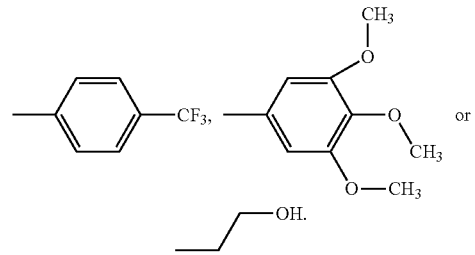

10. A pharmaceutical composition comprising a compound of claim 5, or a phosphate ester, a sulfonate ester, a pharmaceutically acceptable salt, a glycoside derivative, or a solvate thereof.

11. A compound of formula I,

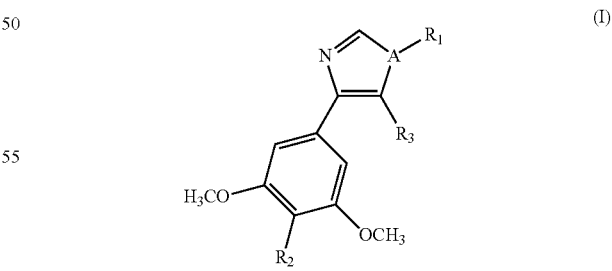

or a phosphate ester, a sulfonate ester, a pharmaceutically acceptable salt, a glycoside derivative or a solvate thereof, wherein
A is N, O or S;
when A is O or S, $R_1$ is absent;
when A is N, $R_1$ is H, $CH_3$, $C_4H_9$,

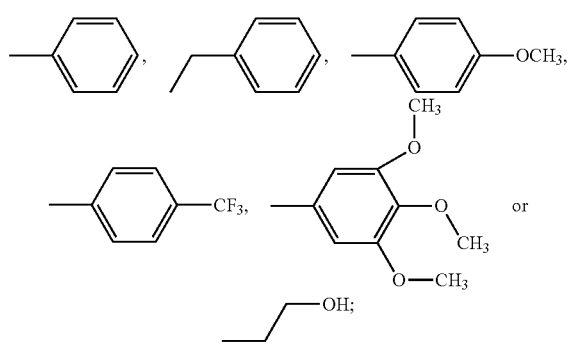
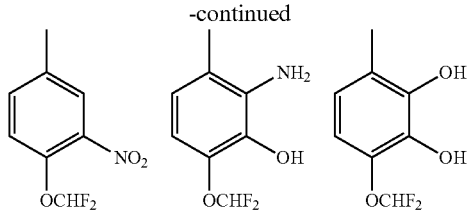
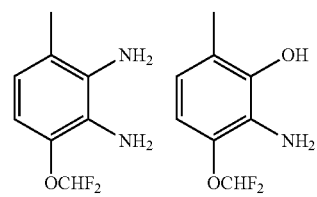
$R_2$ is H, OCH$_3$, NO$_2$, NH$_2$, CF$_3$, OCF$_3$, OCHF$_2$ or —NHCH$_3$; and
$R_3$ is selected from the group consisting of:
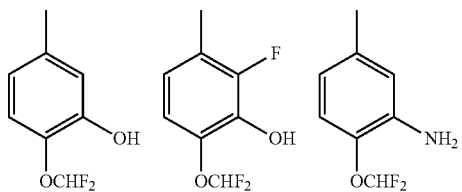
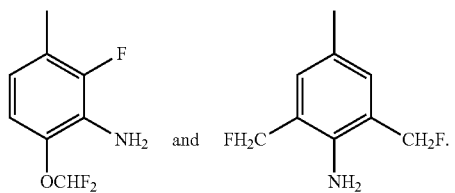
* * * * *